(12) United States Patent
Oda et al.

(10) Patent No.: US 11,045,386 B2
(45) Date of Patent: Jun. 29, 2021

(54) STEAM HEATING MASK

(71) Applicant: KAO CORPORATION, Tokyo (JP)

(72) Inventors: Hideshi Oda, Funabashi (JP); Yasuto Saita, Setagaya-ku (JP); Katsutoshi Hara, Utsunomiya (JP); Keiji Yoshii, Soka (JP)

(73) Assignee: KAO CORPORATION, Tokyo (JP)

( * ) Notice: Subject to any disclaimer, the term of this patent is extended or adjusted under 35 U.S.C. 154(b) by 467 days.

(21) Appl. No.: 15/580,909

(22) PCT Filed: Jun. 10, 2015

(86) PCT No.: PCT/JP2015/066743
§ 371 (c)(1),
(2) Date: Dec. 8, 2017

(87) PCT Pub. No.: WO2016/199245
PCT Pub. Date: Dec. 15, 2016

(65) Prior Publication Data
US 2018/0318166 A1    Nov. 8, 2018

(51) Int. Cl.
*A61H 33/12*    (2006.01)
*A41D 13/11*    (2006.01)
(Continued)

(52) U.S. Cl.
CPC .......... *A61H 33/12* (2013.01); *A41D 13/11* (2013.01); *A61F 7/03* (2013.01); *A62B 18/02* (2013.01)

(58) Field of Classification Search
CPC .......... A41D 13/11; A61F 7/03; A61H 33/12; A61M 16/14; A61M 16/142;
(Continued)

(56) References Cited

U.S. PATENT DOCUMENTS 4,225,542 A * 9/1980 Wall .................. A61M 16/1075
                                                        128/203.12
4,947,924 A * 8/1990 Morita .................... B22D 19/14
                                                        164/103
(Continued)

FOREIGN PATENT DOCUMENTS

CN        1829487 A       9/2006
CN      101146497 A       3/2008
(Continued)

OTHER PUBLICATIONS

Extended European Search Report dated Nov. 13, 2018 in Patent Application No. 15894930.5, 11 pages.
(Continued)

*Primary Examiner* — Jan Christopher L Merene
*Assistant Examiner* — Nathan M Le
(74) *Attorney, Agent, or Firm* — Oblon, McClelland, Maier & Neustadt, L.L.P.

(57) ABSTRACT

A steam heating mask having a mask body portion covering a nose and a mouth of a wearer when wearing the mask, a pair of ear hook portions provided at both left and right ends of the mask body portion, and a steam generator on the mask body portion, in which a proportion of an area occupied by the steam generator ranges from 30% to 80% with respect to an area of an entire surface of the mask body portion on a side of the wearer. The steam generator includes a first sheet on a surface of a steam generating portion on the side of the wearer with degree of air permeability being equal to or less than 7,000 sec/100 ml and a second sheet on a surface opposite to the surface of the steam generating portion with a degree of air permeability being greater than 8,000 sec/100 ml.

8 Claims, 8 Drawing Sheets

(51) Int. Cl.
*A61F 7/03* (2006.01)
*A62B 18/02* (2006.01)
(58) Field of Classification Search
CPC .. A61M 16/145; A61M 16/147; A61M 16/16; A61M 16/161; A62B 18/02
See application file for complete search history.

(56) References Cited

U.S. PATENT DOCUMENTS

| | | | | |
|---|---|---|---|---|
| 5,154,984 | A * | 10/1992 | Morita | C22C 32/00 266/274 |
| 8,333,793 | B2 | 12/2012 | Igaki et al. | |
| 9,084,865 | B2 * | 7/2015 | Nadjafizadeh | A61M 16/021 |
| 2001/0042546 | A1 * | 11/2001 | Umeda | A61F 7/034 128/206.21 |
| 2004/0112366 | A1 * | 6/2004 | Addison | A47C 7/021 126/204 |
| 2004/0149732 | A1 * | 8/2004 | Usui | A61F 7/034 219/528 |
| 2004/0182386 | A1 * | 9/2004 | Meier | A61M 16/024 128/203.12 |
| 2005/0145250 | A1 * | 7/2005 | Miyazawa | A61F 7/03 128/205.25 |
| 2005/0192653 | A1 * | 9/2005 | Tsunakawa | A61F 7/034 607/109 |
| 2006/0154006 | A1 * | 7/2006 | Usui | A61F 7/034 428/34.1 |
| 2007/0020412 | A1 * | 1/2007 | Kumamoto | A61F 7/034 428/34.2 |
| 2009/0062890 | A1 | 3/2009 | Ugajin et al. | |
| 2009/0223514 | A1 * | 9/2009 | Smith | A61M 16/1075 128/203.14 |
| 2010/0010598 | A1 * | 1/2010 | Igaki | A61F 7/034 607/109 |
| 2010/0023099 | A1 * | 1/2010 | Hidaka | A61F 7/034 607/108 |
| 2010/0241199 | A1 * | 9/2010 | Hidaka | A61F 7/034 607/96 |
| 2011/0190714 | A1 * | 8/2011 | Oda | A61F 7/03 604/291 |
| 2011/0209711 | A1 * | 9/2011 | Brillat | A62B 23/025 128/206.19 |
| 2012/0017905 | A1 * | 1/2012 | Sata | A61M 16/1075 128/203.26 |
| 2013/0079851 | A1 * | 3/2013 | Tagami | A61F 7/034 607/96 |
| 2015/0059771 | A1 | 3/2015 | Duffy | |

FOREIGN PATENT DOCUMENTS

| | | |
|---|---|---|
| CN | 104510031 A | 4/2015 |
| EP | 2 111 830 A1 | 10/2009 |
| EP | 2 177 184 A1 | 4/2010 |
| JP | 11-137618 A | 5/1999 |
| JP | 2000-288105 | 10/2000 |
| JP | 2001-29493 A | 2/2001 |
| JP | 2004-73828 A | 3/2004 |
| JP | 2004-321737 | 11/2004 |
| JP | 2006-102145 A | 4/2006 |
| JP | 2007-289682 A | 11/2007 |
| JP | 2009-200 A | 1/2009 |
| JP | 2009-213888 A | 9/2009 |
| JP | 2010-51690 A | 3/2010 |
| JP | 2011-136060 A | 7/2011 |
| JP | 2011-188947 A | 9/2011 |
| JP | 2011-206222 A | 10/2011 |
| JP | 2012-20175 A | 2/2012 |
| JP | 2014-140774 A | 8/2014 |
| RU | 2 515 535 C2 | 5/2014 |
| WO | WO99/51174 | 10/1999 |
| WO | WO 2009/145134 A1 | 12/2009 |
| WO | WO 2011/084290 A2 | 7/2011 |

OTHER PUBLICATIONS

Combined Office Action and Search Report dated Jun. 4, 2019 in Chinese Patent Application No. 201580080790.1 (with partial English translation and English translation of category of cited documents), 10 pages.

International Search Report dated Jul. 14, 2015 in PCT/JP2015/066743 filed Jun. 10, 2015.

Combined Russian Office Action and Search Report dated Dec. 6, 2018 in Patent Application No. 2018100099 (with English tanguage translation).

Office Action dated Apr. 24, 2018 in corresponding Japanese Patent Application No. 2017-523026, 6 pages.

Notice of Allowance dated Jul. 31, 2018 in Japanese Application No. 2017-523026, 3 pages.

Taiwanese Search Report dated Jan. 30, 2020, in Patent Application No. 105130431, 2 pages (with English Translation of Category of Cited Documents).

Office Action in corresponding Chinese Patent Application No. 201580080790, dated Jan. 18, 2021. (w/English Translation).

Office Action in corresponding Japanese Patent Application No. 2020-057416, dated Apr. 6, 2021.

* cited by examiner

STEAM HEATING MASK

TECHNICAL FIELD

The present invention relates to a steam heating mask.

BACKGROUND ART

It is known that a mask blocks dusts, pollen, and the like in an outside air by covering a mouth and nose, and has preventive effects such as allergic rhinitis and colds. In recent years, various functions of the mask covering the mouth and the nose are diversified, and various masks are developed. Among these, it is studied to improve an effect of the mask by incorporating a heating element into the mask to impart a function of warming the nose and cheek.

For example, Patent Document 1 discloses a mask provided with a heating sheet or a heat-retaining sheet. In addition, Patent Document 2 discloses a mask in which a heating element is provided at a position spaced apart from a longitudinal center line of a mask body portion to the left and right. Furthermore, Patent Document 3 discloses a nasal thermal tool in which a heating element generating steam is accommodated inside a mask, and the heating element expands to be in close contact with the nose due to the generated steam.

RELATED DOCUMENT

Patent Document
[Patent Document 1] Japanese Unexamined Patent Publication NO. 2009-200
[Patent Document 2] Japanese Unexamined Patent Publication NO. 2006-102145
[Patent Document 3] Japanese Unexamined Patent Publication NO. 2011-136060
[Patent Document 4] Japanese Unexamined Patent Publication NO. 2004-73828

SUMMARY OF THE INVENTION

Technical Problem

The present invention provides a steam heating mask (first invention) that includes a mask which includes a mask body portion covering a nose and a mouth of a wearer when wearing the mask, and a pair of ear hook portions provided at both left and right ends of the mask body portion, and a steam generator on the mask body portion, in which a proportion of an area occupied by the steam generator is equal to or greater than 30% and equal to or less than 80% with respect to an area of an entire surface of the mask body portion on a side of the wearer, the steam generator accommodates inside a steam generating portion, the steam generator includes a first sheet on a surface of the steam generating portion on the side of the wearer, and a second sheet on a surface opposite to the surface on the side of the wearer, of the steam generating portion, a degree of air permeability of the first sheet is equal to or less than 7,000 sec/100 ml, and a degree of air permeability of the second sheet is greater than 8,000 seconds/100 ml.

In addition, the present invention provides a steam heating mask (second invention) that includes a mask which includes a mask body portion covering a nose and a mouth of a wearer when wearing the mask, and a pair of ear hook portions provided at both left and right ends of the mask body portion, and a steam generator on the mask body portion, in which a proportion of an area occupied by the steam generator is equal to or greater than 30% and equal to or less than 80% with respect to an area of an entire surface of the mask body portion on a side of the wearer, the steam generator accommodates inside a steam generating portion, the steam generator includes a first sheet on a surface of the steam generating portion on the side of the wearer, and a second sheet on a surface opposite to the surface on the side of the wearer, of the steam generating portion, a degree of air permeability of the second sheet is equal to or greater than 250 sec/100 ml and equal to or less than 8,000 sec/100 ml, and a degree of air permeability of the first sheet is equal to or less than 20% with respect to the degree of air permeability of the second sheet.

BRIEF DESCRIPTION OF THE DRAWINGS

The above and other objects, advantages and features will be more apparent from the following description of the preferred embodiments and the accompanying drawings.

DESCRIPTION OF EMBODIMENTS

Figure 1:
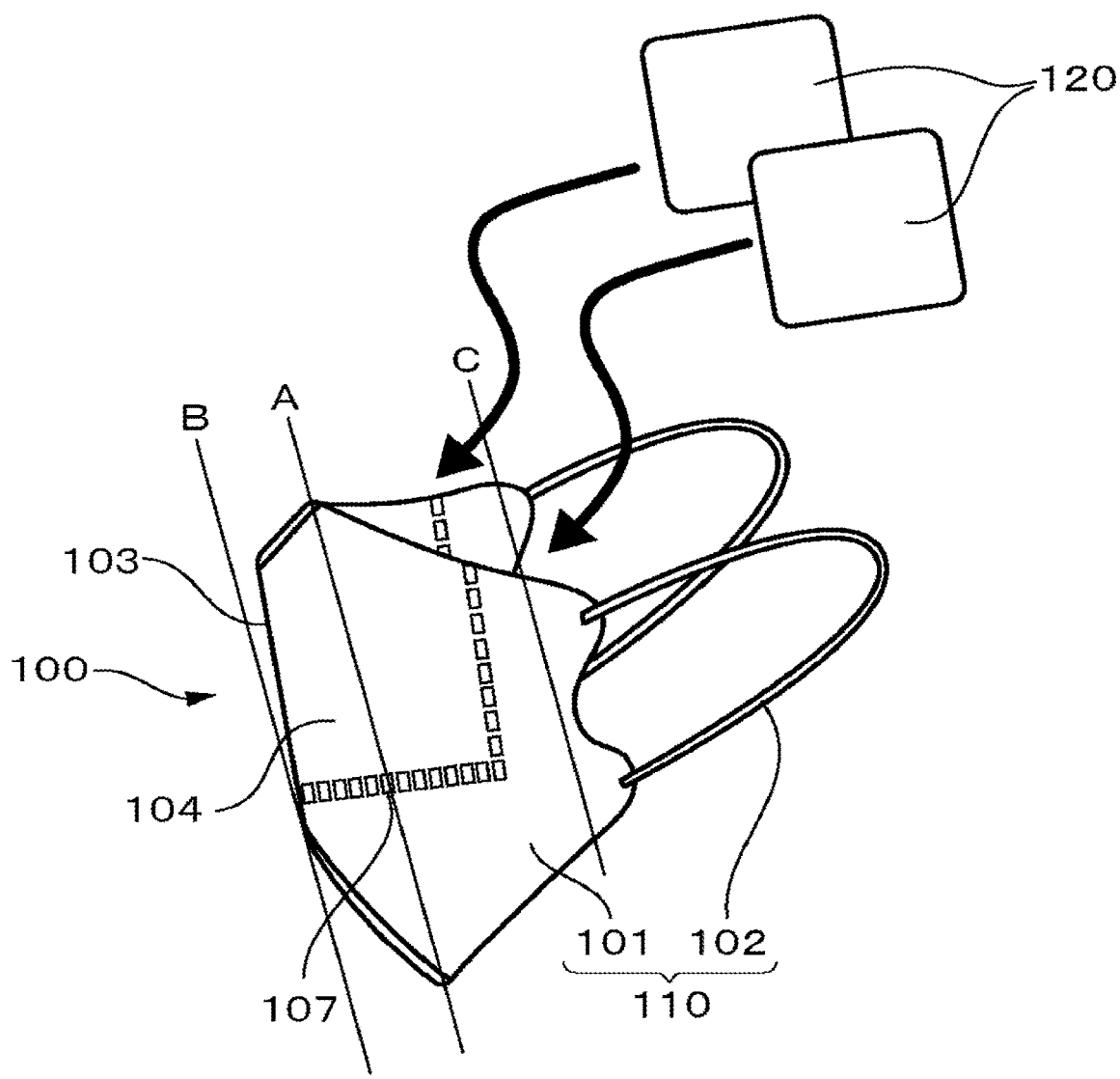
FIG. 1 is a perspective view showing an example of a steam heating mask.

The present inventors have studied the problem of improving an effect of moisturizing mucous membranes of throat and nose by inhaling air that can be easily breathed, positively generate steam heated in the mask, and have an increased absolute humidity in the mask.

The present inventors studied the techniques described in the above-described patent documents, and as a result, it was found that since a mask having a heat generating function as disclosed in Patent Document 1 is intended for heating and does not positively generate the steam, it is impossible to sufficiently raise the absolute humidity in the mask.

In addition, although Patent Document 2 describes that a heating element generates steam, a proportion of an area of a region where the heating element is provided is low with respect to an area of the mask surface, and there is a tendency that sufficient heat generation effect and steam generation effect cannot be obtained.

In addition, Patent Document 3 describes that a heating element generates steam. However, air permeability of the sheet provided on the side of the heating element opposite to the side of a wearer is set to high, and oxygen in the air is positively taken into the heating element to promote an oxidation reaction, so that the heating element is designed to swell by the generated steam. As a result, a mask is brought into close contact with a cheek portion or nose portion with a soft touch to eliminate a gap, and absolute humidity inside the mask is not increased.

Furthermore, Patent Document 4 describes a steam generator that supplies a large amount of steam to the skin, and a method of using the steam generator as a steam mask is disclosed. However, the proportion of an area of a region where the heating element is provided tends to be high with respect to an area of the mask body portion, and a basis weight of the mask body portion is high and the air permeability is low. Therefore, there is room for improvement in feeling of stuffiness when wearing the mask for a long time.

Therefore, in the techniques disclosed in Patent Documents 1 to 4, it was found in any of techniques that there is room for improvement from the viewpoint of solving the problem of improving the effect of moisturizing the mucous membranes of the throat and nose by inhaling the air that can be easily breathed, positively generate the steam heated in the mask, and have the increased absolute humidity in the mask.

The present inventors studied means which solves the above problems, and as a result, it was found that a steam heating mask that can be easily breathed, positively generate steam heated in a mask, increase an absolute humidity in the mask, and improve moist feeling of mucous membranes of a throat and nose can be provided by adopting a configuration of an area proportion occupied by a steam generator in the mask body portion, and the steam generator which adopts a configuration of specific sheet.

According to the present invention, there is provided a steam heating mask that can be easily breathed, positively generate steam heated in a mask, increase an absolute humidity in the mask, and improve moist feeling of mucous membranes of a throat and nose.

Hereinafter, embodiments of the present invention will be described with reference to the drawings.

In all the drawings, similar components are denoted by the same reference numerals, and description thereof will not be appropriately repeated.

In addition, in the present specification, "to" represents "equal to or greater than and equal to or less than", unless otherwise specified.

In addition, the structures and elements described in the respective embodiments can be appropriately combined as long as the effects of the invention are not impaired.

In addition, in the present embodiment, a degree of air permeability of a sheet or the like can be measured as follows.

The degree of air permeability is a value measured by JIS P8117 (2009 revised edition) and is defined as a time when 100 ml of air passes through an area of 6.42 cm$^2$ under a fixed pressure. Therefore, a large numerical value of the degree of air permeability means that it takes time to pass through the air, that is, that the air permeability is low. On the contrary, a small numerical value of the degree of air permeability means that the air permeability is high. In this manner, the magnitude of the numerical value of the degree of air permeability, and the high and low of the air permeability show the inverse relationship. The degree of air permeability can be measured by Oken type air permeability meter.

In the present specification, when the degree of air permeability is equal to or greater than 30,000 sec/100 ml, it is treated as "air impermeable", and when the degree is equal to or greater than 80,000 sec/100 ml, it is treated as "non-air permeable".

First Embodiment

The steam heating mask in the present embodiment is shown below.

A steam heating mask includes a mask which includes a mask body portion covering a nose and a mouth of a wearer when wearing the mask, and a pair of ear hook portions provided at both left and right ends of the mask body portion, and a steam generator on the mask body portion, in which a proportion of an area occupied by the steam generator is equal to or greater than 30% and equal to or less than 80% with respect to an area of an entire surface of the mask body portion on a side of the wearer, the steam generator accommodates inside a steam generating portion, the steam generator includes a first sheet on a surface of the steam generating portion on the side of the wearer, and a second sheet on a surface opposite to the surface on the side of the wearer, of the steam generating portion, a degree of air permeability of the first sheet is equal to or less than 7,000 sec/100 ml, and a degree of air permeability of the second sheet is greater than 8,000 seconds/100 ml.

FIG. 1 is a perspective view showing an example of a steam heating mask 100. The steam heating mask 100 is a combination of the mask 110 and the steam generator 120.

Figure 2:
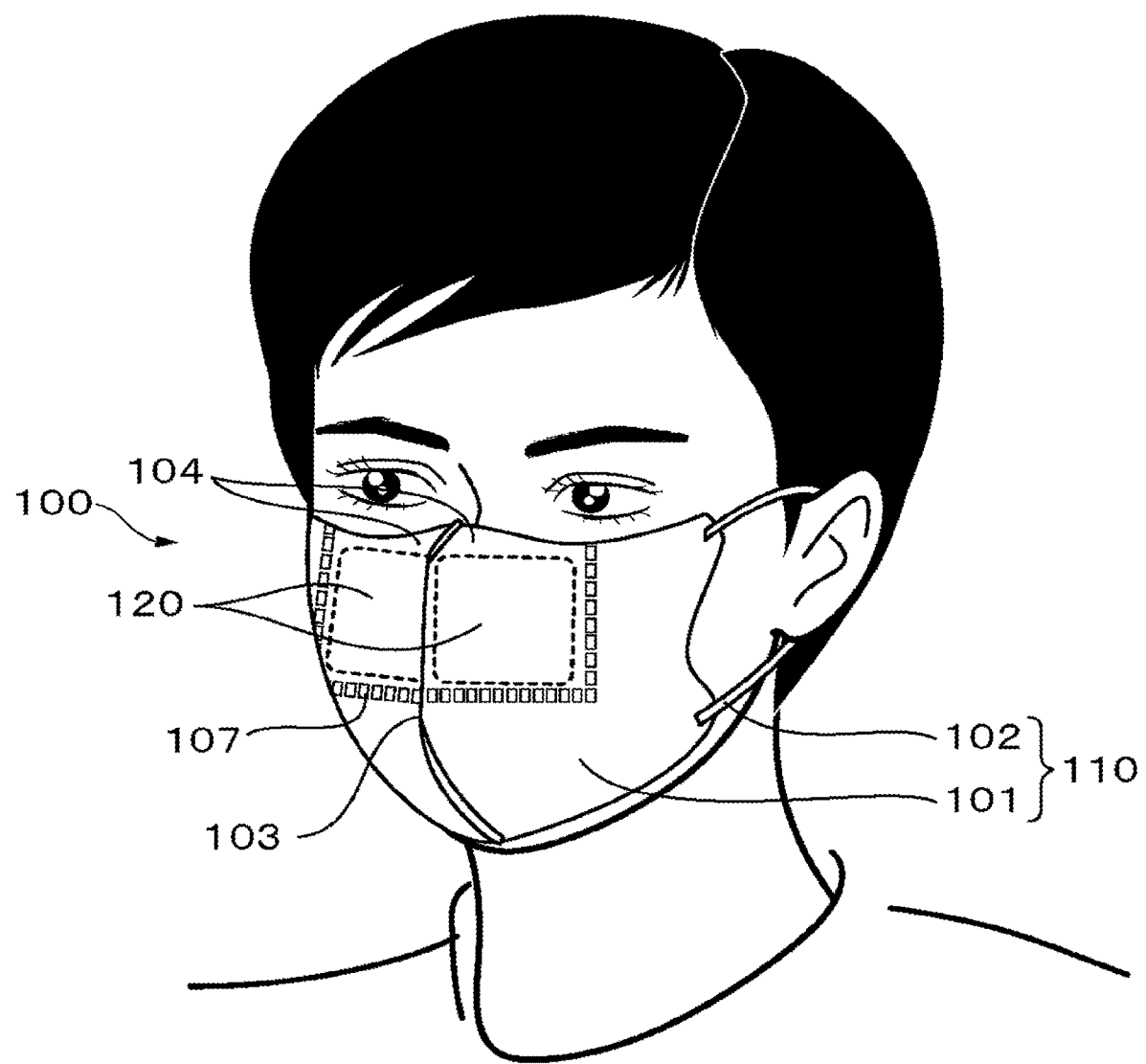
FIG. 2 is a diagram showing an example of a usage state of the steam heating mask.
Figure 3:
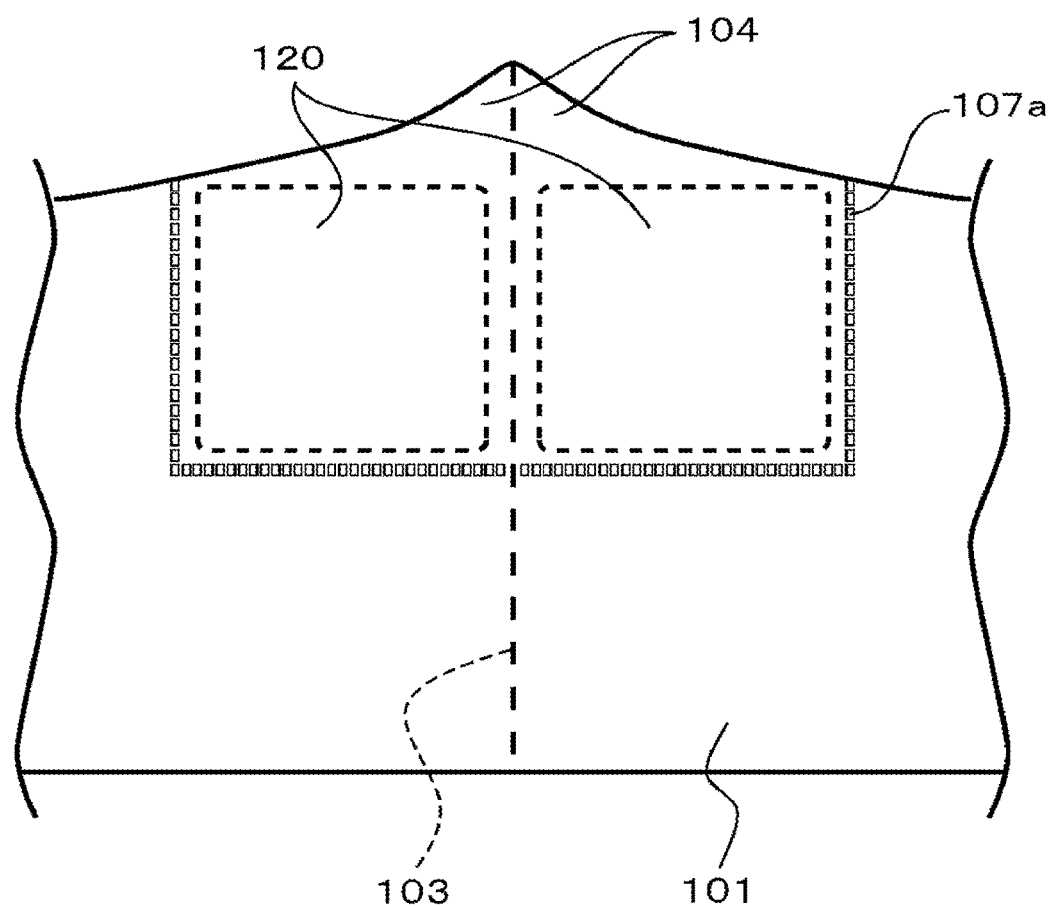
FIG. 3 is a plan view of a portion of a mask seen from a surface on a side of a wearer according to a first embodiment.
Figure 4:
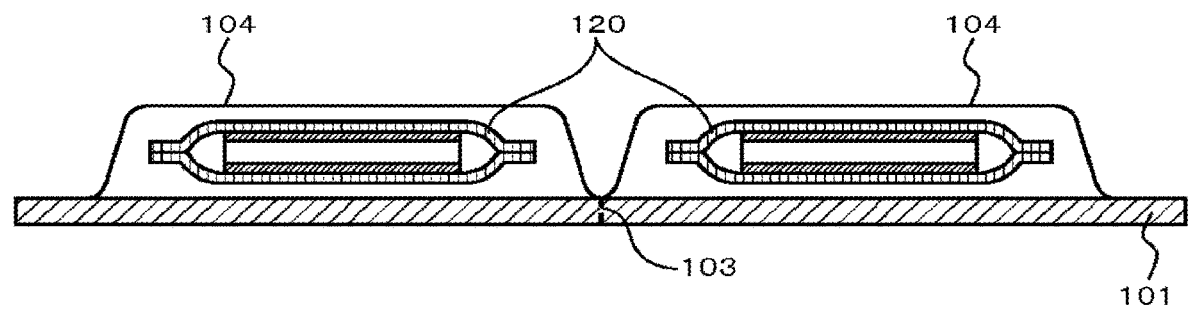
FIG. 4 is a cross-sectional view of the portion of the mask seen from an upper surface (eye side of the wearer) according to the first embodiment.

FIG. 2 is a diagram showing an example of a usage state of the steam heating mask 100. FIG. 3 is a plan view of a portion of a mask 110 seen from a surface on a side of a wearer according to a first embodiment. FIG. 4 is a cross-sectional view of the portion of the mask seen from an upper surface (eye side of the wearer) according to the first embodiment.

In the present embodiment, the steam heating mask 100 is described as a structure in which the mask 110 and the steam generator 120 are separated, and the steam generator 120 can be taken in and out of an accommodation body 104, but the steam heating mask 100 may be a structure in which the steam generator 120 is enclosed inside the accommodation body 104 of the mask 110.

[Mask]

As shown in FIGS. 1 and 2, the mask 110 includes the mask body portion 101 covering the nose and mouth when wearing the mask, and a pair of ear hook portions 102 provided at both left and right ends of the mask body portion 101.

In the present embodiment, the mask 110 is shown as having a folding line 103 at a position corresponding to the nasal bridge of the wearer, but the mask 110 having a flat shape without the folding line 103 may be used in accordance with the application or the like.

Hereinafter, the shape of the mask 110 will be described by exemplifying one having the folding line 103.

In the present embodiment, the mask body portion 101 is in the form of a sheet, and more specifically, is formed from one sheet and folded in a symmetrical manner with the folding line 103. Before use, the mask body portion 101 is folded in a mountain along the folding line 103, and is in a state of being folded flat.

As shown in FIGS. 1 and 2, the folding line 103 has a substantially circular arc shape in which a nose portion is a convex portion, and an upper portion and a lower portion are bonded to each other. The mask body portion 101 is opened from the side opposite to the folding line 103 and is worn so that the surface on the inner side on which the sheets are superposed is the surface on the side of the wearer.

The folding line 103 protrudes forward of the mask body portion 101 when the mask 110 is worn. When the folding line 103 is provided, the upper portion of the mask body portion 101 is in close contact with along the shape of the nose, so that a gap is unlikely to be formed, and the heating and humidifying effect can be enhanced, which is preferable.

The single sheet forming the mask body portion 101 may have a single structure (that is, one ply), or may have an integral structure (that is, multiply) by laminating a plurality of sheets. By using a plurality of sheets, it is preferable from the viewpoint that various functions can be imparted to a covering portion by imparting a separate function to each sheet. In a case of using a plurality of sheets, the respective sheets may be in a laminated state where the sheets are bonded over the entire surface, or may be in a state where the sheets are separated from each other. In addition, in a case where the respective sheets are separated from each other, the sheets may be bonded to each other by sealing the edges of the respective sheets along the shape of the covering portion, or by merely bonding a portion of the edges with a point seal.

In the present embodiment, as shown in FIG. 4, for example, an example in which the mask body portion 101 has a single structure will be described.

As a material of the mask body portion 101, the material used in the technical field of the mask in the related art can be used, and there is no particular limitation on the type as long as the mask has a certain amount of air permeability. For example, a fiber sheet such as a nonwoven fabric and gauze can be used, and it is preferable to use the nonwoven fabric from the viewpoints of ease of processing and economical efficiency. As the fiber material of the nonwoven fabric, for example, the material made of one or more kinds of the fiber selected from polyester such as polyethylene terephthalate (PET); polyolefin such as polyethylene (PE), polypropylene (PP), and ethylene propylene copolymer; rayon; cotton, and the like is preferable. In addition, as the nonwoven fabric, the fabric manufactured by an air-through method, a spun bond method, a needle punch method, a melt blown method, a card method, a thermal fusion method, a hydroentangling method, a solvent adhesion method, or the like can be used, using the fiber of one or more kinds of the above materials.

It is preferable that the mask body portion 101 has an appropriate air permeation resistance from the viewpoint of keeping the steam generated from the steam generator 120 in the mask 110 and facilitating breathing.

Specifically, the air permeation resistance of the mask body portion 101 is preferably equal to or greater than 5 Pa, more preferably equal to or greater than 20 Pa, and still more preferably equal to or greater than 50 Pa. In addition, the air permeation resistance of the mask body portion 101 is preferably equal to or less than 200 Pa, more preferably equal to or less than 190 Pa, and still more preferably equal to or less than 180 Pa.

In addition, the air permeation resistance of the mask body portion 101 is preferably equal to or greater than 5 Pa and equal to or less than 200 Pa, more preferably equal to or greater than 20 Pa and equal to or less than 190 Pa, and still more preferably equal to or greater than 50 Pa and equal to or less than 180 Pa. When the structure of the mask body portion 101 is multiply, it is the air permeation resistance measured in a state where all of the plurality of sheets are superimposed.

The air permeation resistance of the mask body portion 101 can be measured as follows.

Figure 10:
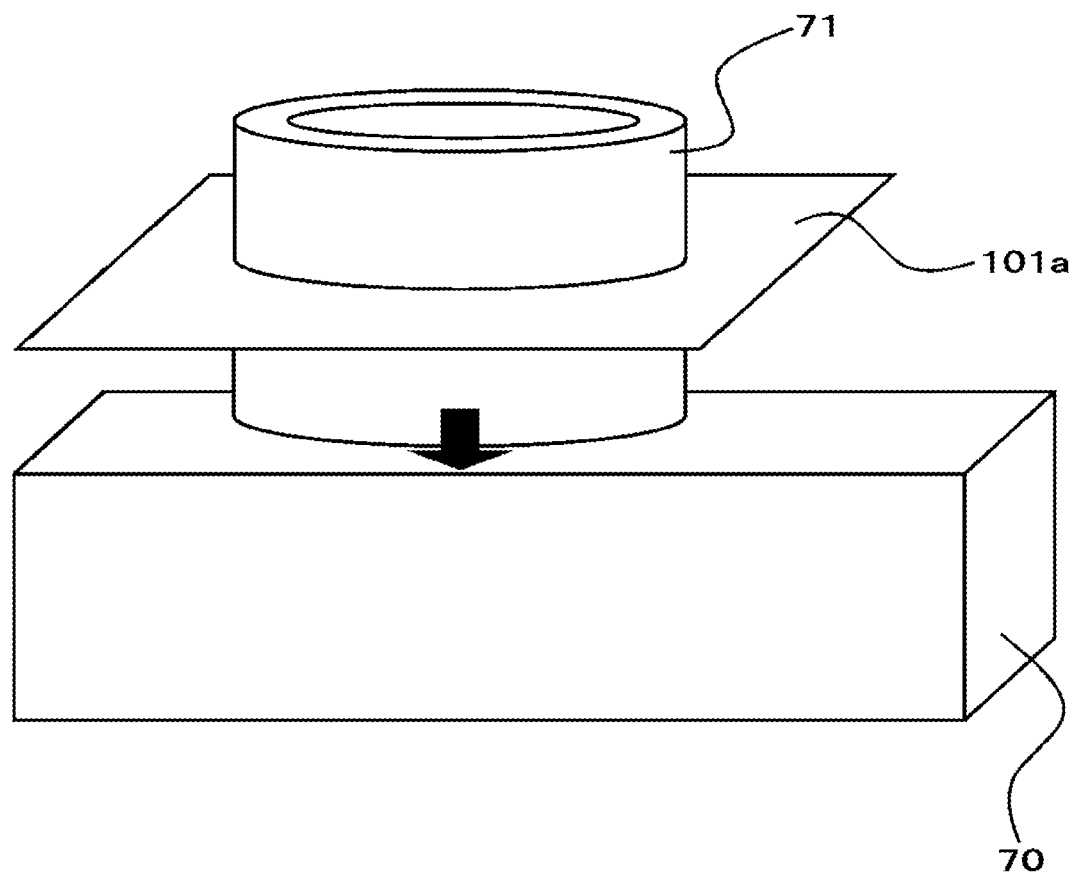
FIG. 10 is a schematic diagram showing an air permeation resistance measuring device.

As shown in FIG. 10, the sheet 101*a* which is cut out into a size of 3.5 to 5 cm square from the sheet material of the mask body portion 101 is disposed on an upper portion of a main body 70 of an evaluating apparatus for air permeation resistance of mask tester MTS-2 (manufactured by Shibata Scientific Co., Ltd.), and is fixed by the sheet fixing jig 71 so as not to leak. The measurement is performed for 10 seconds at a test area of 7 $cm^2$ (inner diameter 30 mm) and a test flow rate of 10 L/min, and the air permeation resistance is obtained from the differential pressure between the air inflow side (inlet side) and the air outflow side (outlet side) to the sheet 101*a*.

From the viewpoint of preventing the inside of the mask 110 from being seen through, or improving the heat retention, flexibility, thickness, sheet strength in a balanced manner, the basis weight of the mask body portion 101 is preferably equal to or greater than 5 $g/m^2$, more preferably equal to or greater than 10 $g/m^2$, and still more preferably equal to or greater than 30 $g/m^2$. In addition, the basis weight is preferably equal to or less than 200 $g/m^2$, more preferably equal to or less than 150 $g/m^2$, and still more preferably equal to or less than 120 $g/m^2$. In addition, the basis weight is preferably equal to or greater than 5 $g/m^2$ and equal to or less than 200 $g/m^2$, more preferably equal to or greater than 10 $g/m^2$ and equal to or less than 150 $g/m^2$, and still more preferably equal to or greater than 30 $g/m^2$ and equal to or less than 120 $g/m^2$.

In the present embodiment, the steam heating mask 100 is provided with the steam generator 120. The steam generator 120 may be incorporated in the mask body portion 101, or may have a fixing means for fixing the steam generator 120 to the mask body portion 101 and may be fixedly used at the time of use, but in the present embodiment, the steam generator 120 is fixed at the time of use. In the embodiment shown in FIGS. 1 and 2, the mask body portion 101 is provided with the accommodation body 104 on the surface on the side of the wearer by a seal portion 107. The accommodation body 104 accommodates the steam generator 120 in a freely removable manner. As a result, after using the mask 110, the mask 110 can be used many times by replacing the steam generator 120 with another steam generator 120 before use.

For example, as shown in FIG. 3, the accommodation body 104 can be formed by the seal portion 107*a* that surrounds the outer periphery except for the upper portions of the two steam generators 120 arranged in the lateral direction. Specifically, a method of overlapping sheets constituting the accommodation body 104 on the surface of the mask body portion 101 on the side of the wearer and sealing the seal portion 107*a* shown in FIG. 3 by thermal fusion or the like, a method of overlapping the sheets constituting the accommodation body 104, sealing the portion of the folding line 103 at the longitudinal central portion of the mask body portion 101, and thereafter sealing the seal portion 107a shown in FIG. 3 when preparing the mask body portion 101, and the like are included. As a result, it is possible to form the pocket-like accommodation body 104 into which the steam generator 120 can be inserted from above the mask body portion 101.

Figure 5:
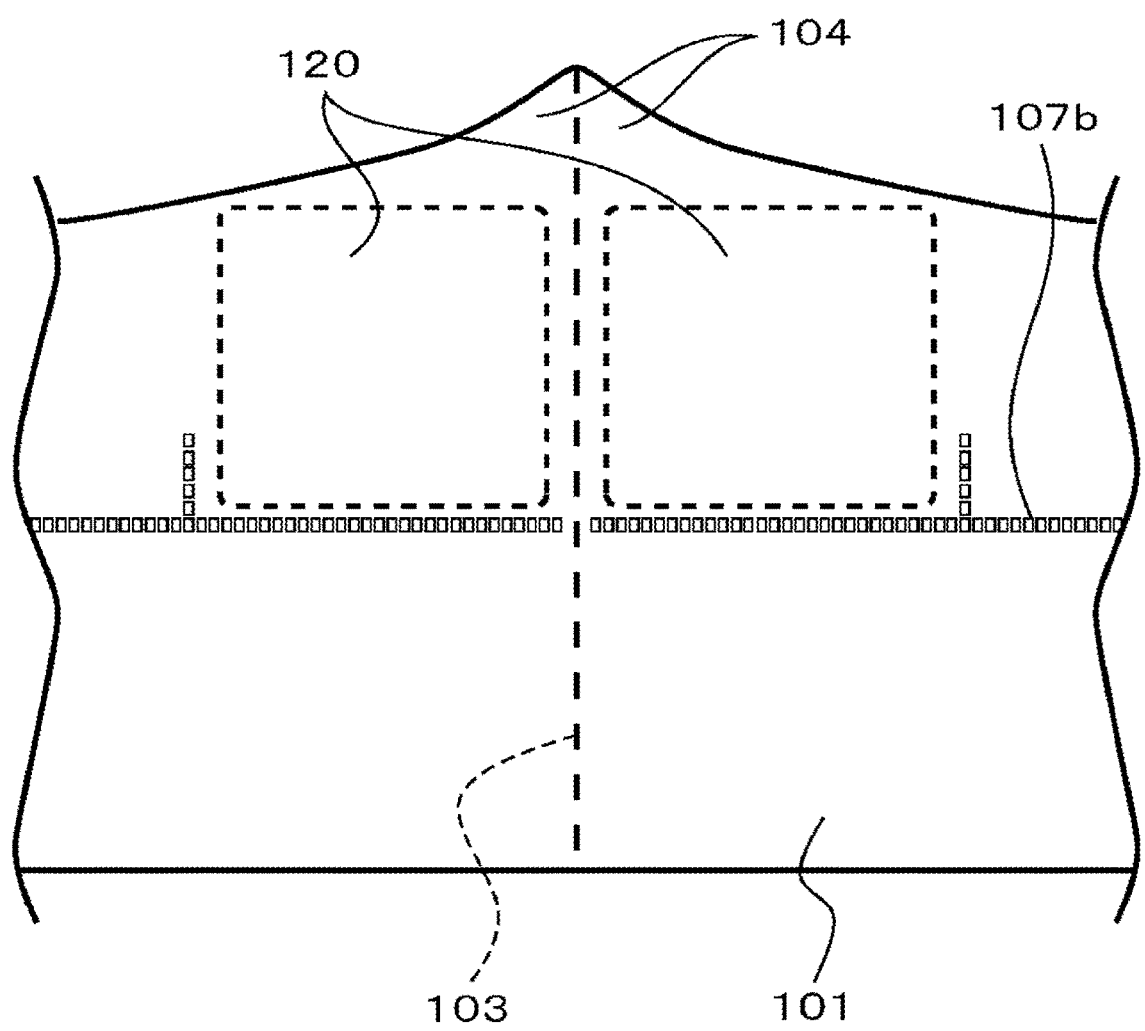
FIG. 5 is a plan view of a modified example of the mask seen from the surface on the side of the wearer according to the first embodiment.
Figure 6:
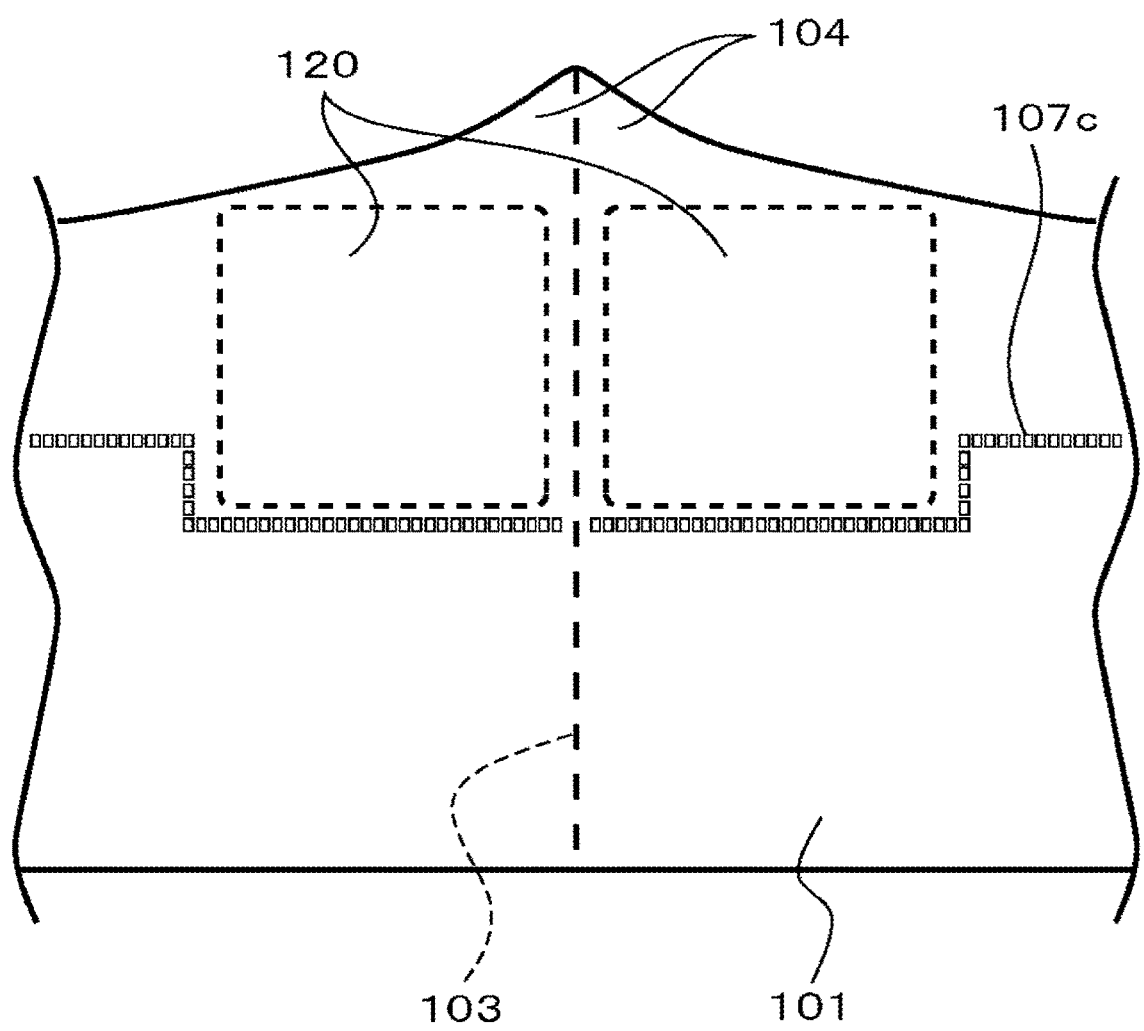
FIG. 6 is a plan view of a modified example of the mask seen from the surface on the side of the wearer according to the first embodiment.

The method for forming the accommodation body 104 is not limited thereto. FIGS. 5 and 6 are plan views of modified examples of the mask seen from the surface on the side of the wearer according to the first embodiment. That is, as shown in FIGS. 5 and 6, the accommodation body 104 may be formed by the sheet constituting the mask body portion 101, and a seal portion 107b or a seal portion 107c to which the sheet constituting the a accommodation body 104 is fixed at a position where a portion of the lower portion of the steam generator 120 is fixed. In FIG. 5, the seal portion 107b including a straight line and extending so as to be in contact with the lower portion of the steam generator 120 and a longitudinal straight line extending in a portion of the lower portion of the side surface of the steam generator 120 on the ear hook portion 102 side is shown in the lateral direction of the central portion of the mask body portion 101. In FIG. 6, a deformed linear seal portion 107c is shown along the shape of the lower portion of the steam generator 120 in a lateral direction slightly above the central portion of the mask body portion 101.

In the present embodiment, it is preferable that the accommodation body 104 is fixed in the vicinity of the folding line 103 of the mask body portion 101 and in the vicinity of the upper end of the mask body portion 101 from the viewpoint that the steam generator 120 can be fixed to the mask body portion 101 at a predetermined position, and the space inside the mask 110 from the nose to the cheek of the wearer can be easily heated and humidified.

In the present embodiment, the accommodation body 104 has an opening so that the steam generator 120 can be taken in and out to the upper end portion or the ear hook portion 102 side, and the other end portion thereof is fixed to the mask body portion 101. The position of the opening portion is not particularly limited as long as the steam generator 120 does not take out from the accommodation body 104 when the mask 110 is worn. In addition, the size of the accommodation body 104 may be any size as long as the accommodation body 104 can fix the position of the steam generator 120 while accommodating the steam generator 120.

The accommodation body 104 has the air permeability and can be made of the same material as the mask body portion 101. From the viewpoint of effectively imparting the heating and humidifying performance by the steam generator 120 to the mask 110 while preventing excessive heat generation, the air permeation resistance of the accommodation body 104 is preferably equal to or greater than 1 Pa and equal to or less than 100 Pa, more preferably equal to or greater than 1 Pa and equal to or less than 50 Pa, and still more preferably equal to or greater than 1 Pa and equal to or less than 30 Pa.

The ear hook portions 102 are used in pairs and are provided at each of left and right end portions in the longitudinal direction (X direction) of the mask body portion 101.

In the present embodiment, as shown in FIGS. 1 and 2, the ear hook portion 102 is described with reference to an example in which a cord-like material having elasticity such as a rubber string is formed at the end portion of the mask body portion 101, but a member having elasticity integrated with the mask body portion 101 may be used.

The ear hook portion 102 may be made of the same material as the mask body portion 101 or may be a different material.

[Steam Generator]

The steam generator 120 is attached to the mask body portion 101.

The present inventors studied, and as a result, it was found that the area of the steam generator 120 in the planar shape is set to a specific proportion with respect to the area of the entire surface of the mask body portion 101 on the side of the wearer, and in addition to this, the steam generator 120 is configured using a sheet having a specific degree of air permeability. Therefore, adequately generated steam can be retained inside the mask 110, and the air permeability of the mask 110 can be ensured to the extent that the wearer does not feel stuffy.

From the viewpoint of increasing the absolute humidity inside the mask 110 when using the mask, the proportion of the area occupied by the steam generator 120 with respect to the area of the entire surface of the mask body portion 101 on the side of the wearer is equal to or greater than 30%, preferably equal to or greater than 40%, and more preferably equal to or greater than 45%.

In addition, from the viewpoint of ensuring adequate air permeability as the mask 110, the proportion of the area occupied by the steam generator 120 with respect to the area of the entire surface of the mask body portion 101 on the side of the wearer is equal to or less than 80%, preferably equal to or less than 70%, and more preferably equal to or less than 65%.

From the same viewpoint, the proportion of the area occupied by the steam generator 120 with respect to the area of the entire surface of the mask body portion 101 on the side of the wearer is equal to or greater than 30% and equal to or less than 80%, preferably equal to or greater than 40% and equal to or less than 70%, and more preferably equal to or greater than 45% and equal to or less than 65%.

Here, the area of the entire surface of the mask body portion 101 on the side of the wearer is the entire area of the sheet constituting the mask body portion 101, refers to the entire surface including the region of the provided steam generator 120, and is not an area including the ear hook portion 102.

More specifically, when folding the mask at the center in the longitudinal direction, a point on the folding line which is farthest from a line (A line) connecting upper and lower points that are farthest apart from each other vertically in the direction of the tip end is set as a tip end of the mask, and the area refers to the portion from a line (B line) parallel to the A line passing through the tip end of the mask to a line (C line) spaced in parallel by 7 cm in the direction of the ear hook. In addition, in a case where the folded portion of the tip end of the mask is in close contact by heat sealing or the like, the distance is measured with the end of the seal width portion on the ear hook side as the tip end. Furthermore, in a case of a pleated mask, the mask is folded symmetrically in a state where the mask is stretched upward and downward and the crease portion of the mask central portion is extended, and the distance is measured, but at this time, the crease portion of the pleat remaining on the ear hook side from the tip end of the mask is not added to the area.

Even in a case where the ear hook portion 102 is made of a fiber sheet or the like, this region is not included in the area of the entire surface of the mask body portion 101 on the side of the wearer.

On the other hand, the area of the steam generator 120 is the area in the planar shape of a bag body 122 that accommodates a steam generating portion 121, which will be described later, and refers to the area including the seal portion of the sheet constituting the bag body.

In the present embodiment, the steam generator 120 is attached to the mask body portion 101. From the viewpoint that a space surrounded by the depression of the face between the nose portion and the cheek portion and the steam generator 120 is generated on the skin side of the mask body portion 101 when wearing the mask, and the temperature and the absolute humidity inside the mask 110 are increased without suppressing the generation of steam, as shown in FIGS. 1 and 2, the position of the steam generator 120 is preferably attached symmetrically in the vicinity of the folding line 103 of the mask body portion 101 and in the vicinity of the upper end of the mask body portion 101. The vicinity of the folding line 103 and the vicinity of the upper end portion of the mask body portion 101 are not limited to a case of being in contact with the folding line 103 and the upper end portion of the mask body portion 101, indicate a region around the folding line 103 and the upper end portion of the mask body portion 101, and are a region where the steam generator 120 attached to the mask body portion 101 covers the nose portion of the wearer. In addition, the steam generator 120 may reach the cheek portion of the wearer, but it is preferable that the steam generator 120 does not cover only the cheek portion from the viewpoint that a space surrounded by the depression of the face between the nose portion and the cheek portion and the steam generator 120 is generated on the skin side of the mask body portion 101 when wearing the mask, and the temperature and the absolute humidity inside the mask 110 are increased without suppressing the generation of steam.

From the viewpoint of increasing the temperature and the absolute humidity inside the mask 110 without suppressing the generation of steam when the mask 110 is attached, in a case where the nose-side end portion of the steam generator 120 is linear, the position of the steam generator 120 is preferably such that an average of the shortest distances from the folding lines 103 at both ends of the straight line, and in a case where the nose-side end portion of the steam generator 120 is curved, the position of the steam generator 120 is preferably such that the shortest distance from the folding line 103 of the curve is equal to or less than 15 mm, more preferably equal to or less than 10 mm, and still more preferably equal to or less than 5 mm. In addition, from the same viewpoint, the position of the steam generator 120 is preferably such that the shortest distance from the upper end portion of the mask body portion 101 at the upper end portion of the steam generator 120 is equal to or less than 15 mm, more preferably equal to or less than 10 mm, and still more preferably equal to or less than 5 mm.

In addition, the planar shape of the steam generator 120 is not particularly limited, and may be circular, polygonal, or the like. From the viewpoints of manufacturing efficiency, ease of handling, heating and humidifying effect, a square such as a rectangle, a substantially square or the like is preferable, and from the viewpoint of ease of handling, the substantially square is more preferable. In addition, in a case where the nose-side end portion of the steam generator 120 is linear, it is preferable that a portion of the folding line 103 of the mask body portion 101 being in contact with the steam generator 120 is linear.

In addition, from the viewpoint of maintaining the shape of the mask and improving the absolute humidity inside the mask, and from the viewpoint of preventing the feeling of stuffiness due to the mask adhering to the skin around the nose and inhabitation of ventilation with an inhalation, a stiffness value in the vertical direction of the steam generator 120 measured under the following conditions is preferably equal to or greater than 30 gf/60 mm width, more preferably equal to or greater than 60 gf/60 mm width, and still more preferably equal to or greater than 70 gf/60 mm width.

In addition, from the viewpoint of improving comfort during wearing, the stiffness value in the vertical direction of the steam generator 120 is preferably equal to or less than 150 gf/60 mm width, more preferably equal to or less than 130 gf/60 mm width, and still more preferably equal to or less than 120 gf/60 mm width.

In addition, the stiffness value in the vertical direction of the steam generator 120 measured under the following conditions is preferably equal to or greater than 30 gf/60 mm width and equal to or less than 150 gf/60 mm width, more preferably equal to or greater than 60 gf/60 mm width and equal to or less than 130 gf/60 mm width, and still more preferably equal to or greater than 70 gf/60 mm width and equal to or less than 120 gf/60 mm width.

[Stiffness Value Measurement Condition]

The steam generator is supported at a span distance of 30 mm using a Tensilon universal testing machine (ORIENTEC RTC-1150A), and a load is applied to the center of the test piece (steam generator) at a cross head speed of 20 mm/min with a plate-like pressing member having a width of 60 mm and a tip radius of 5 mm. The peak load (average value of three measurements) at this time is defined as the stiffness value.

For this measurement, the steam generator 120 itself may be used as a measurement sample, or the mask 110 accommodating the steam generator 120 may be used as a measurement sample.

Figure 9:
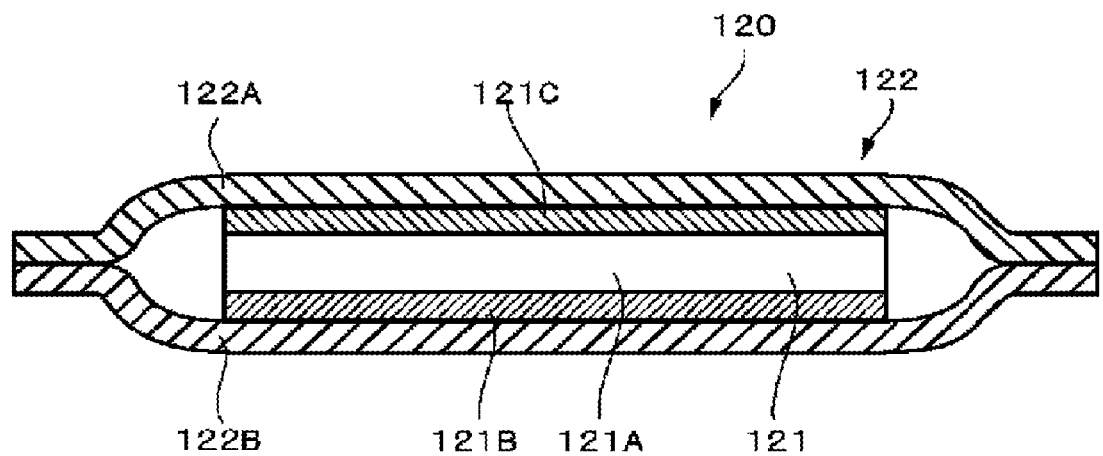
FIG. 9 is a cross-sectional view showing an example of the steam generator.

As shown in FIG. 9, the steam generator 120 accommodates the steam generating portion 121 therein. In the present embodiment, the steam generator 120 has a steam generating portion 121 and the bag body 122 that accommodates the steam generating portion 121. The bag body 122 is provided with a first sheet 122A on a surface of a side (skin side) of the wearer and a second sheet 122B on a surface opposite to the surface of the side (skin side) of the wearer.

The steam generator 120 generates heat while generating the steam by reacting with oxygen in the air.

In a case where the steam generator 120 can be attached to and detached from the mask 110, the steam generator 120 is contained in an oxygen blocking bag before use.

The oxygen blocking bag has an oxygen barrier property as a whole, so that the steam generator 120 does not come into contact with oxygen in the air. As a material having an oxygen barrier property of the oxygen blocking bag, for example, an oxygen permeability coefficient (ASTM D 3985) thereof is preferably equal to or less than 10 $cm^3 \cdot mm/(m^2 \cdot day \cdot MPa)$, and particularly preferably equal to or less than 2 $cm^3 \cdot mm/(m^2 \cdot day \cdot MPa)$. Specific examples thereof include films such as ethylene-vinyl alcohol copolymer and polyacrylonitrile, and films obtained by vapor-depositing ceramic, aluminum, or the like on such films.

In addition, in a case where the steam generator 120 is enclosed in the mask 110, the entire mask 110 may be enclosed in the oxygen blocking bag so as to avoid contact between the steam generator 120 and oxygen in the air.

The steam generating portion 121 may take various forms. The steam generating portion 121 may be, for example, any of a sheet form such as a powder mixture or a papermaking sheet, or a coated sheet obtained by applying dispersion or the like on a substrate.

The steam generating portion 121 may include an oxidizable metal, a water absorbing agent, water, an electrolyte, and, if necessary, a reaction promoter, and the like.

When the steam generating portion 121 comes into contact with air, an oxidation reaction of the oxidizable metal contained therein occurs, and heat is generated. By this heat, the water contained in the steam generating portion 121 is heated to be steam of a predetermined temperature, and is discharged to the outside through the bag body 122. The steam is discharged to the outside from an air permeable portion of the bag body 122.

The oxidizable metal is a metal that generates heat of oxidation reaction, and examples thereof include one or more kinds of powders or fibers selected from iron, aluminum, zinc, manganese, magnesium, and calcium. Among these, iron powder is preferable from the viewpoints of ease of handling, safety, manufacturing cost, storage stability, and stability. Examples of the iron powder include one or more kinds selected from reduced iron powder and atomized iron powder.

In a case where the oxidizable metal is powder, from the viewpoint that the oxidation reaction is efficiently performed, the average particle diameter thereof is preferably equal to or greater than 0.1 μm, more preferably equal to or greater than 10 μm, and still more preferably equal to or greater than 20 μm. From the same viewpoint, it is preferably equal to or less than 300 μm, more preferably equal to or less than 200 μm, and still more preferably equal to or less than 150 μm.

Furthermore, from the viewpoint of improving the coatability, the average particle diameter is preferably equal to or greater than 10 μm and equal to or less than 200 μm, and the average particle diameter is more preferably equal to or greater than 20 μm and equal to or less than 150 μm.

In addition, from the viewpoint of improving the fixability of fibrous materials and the like to a water retaining material and the control of the reaction, it is preferable to use those having a particle diameter of 0.1 to 150 μm in an amount of equal to or greater than 50% by mass.

The particle diameter of the oxidizable metal refers to the maximum length in the form of powder, and is measured by a classification with a sieve, a dynamic light scattering method, a laser diffraction method, or the like.

The content of the oxidizable metal in the steam generating portion 121 is preferably equal to or greater than 100 $g/m^2$, and more preferably equal to or greater than 200 $g/m^2$ in terms of basis weight. In addition, the content of the oxidizable metal in the steam generating portion 121 is preferably equal to or less than 3,000 $g/m^2$, and more preferably equal to or less than 1,600 $g/m^2$, represented in the basis weight.

In addition, the content is preferably equal to or greater than 100 $g/m^2$ and equal to or less than 3,000 $g/m^2$, and more preferably equal to or greater than 200 $g/m^2$ and equal to or less than 1,600 $g/m^2$. As a result, the heat generation temperature of the steam generator 120 can be raised to a desired temperature.

Here, the content of the oxidizable metal can be determined by an ash test according to JIS P8128 or a thermogravimetric instrument. In addition, the content can be quantified by a magnetization measurement test with vibration sample type, or the like utilizing the property that magnetization occurs when an external magnetic field is applied.

As the water absorbing agent, the type thereof is not particularly limited as long as the water absorbing agent can hold water, and examples thereof include one or more kinds selected from a carbon component, a fibrous material, a water absorbent polymer, and a water absorbent powder. As the water absorbing agent, an appropriate agent is used according to the form of the steam generating portion 121.

As the carbon component, one having water retention capability, oxygen supply capability, and catalytic capability can be used, and for example, one or more kinds selected from activated carbon, acetylene black, and graphite can be used. Among these, activated carbon is preferable, and one or more kinds of fine powdery substances or small granular substances selected from coconut shell carbon, wood charcoal, and peat coal are more preferable. Among these, the wood charcoal is still more preferable from the viewpoint of obtaining a favorable heating and humidifying effect.

The water absorbing agent preferably has an average particle diameter of equal to or greater than 10 μm, and more preferably equal to or greater than 12 μm. In addition, the water absorbing agent preferably has an average particle diameter of equal to or less than 200 μm, and more preferably equal to or less than 100 μm.

In addition, the water absorbing agent preferably has an average particle diameter of equal to or greater than 10 μm and equal to or less than 200 μm, and more preferably has an average particle diameter of equal to or greater than 12 μm and equal to or less than 100 μm.

The average particle diameter of the water absorbing agent refers to the maximum length in the form of powder, and is measured by a dynamic light scattering method, a laser diffraction method, or the like. It is preferable to use a powdery form of the carbon component, but it is possible to use a form other than the powdery form, and for example, a fibrous form can be used.

As the fibrous material, natural or synthetic fibrous materials can be used without particular limitation.

Examples of natural fibrous materials include vegetable fibers such as cotton, kapok, wood pulp, non-wood pulp, peanut protein fiber, corn protein fiber, soy protein fiber, mannan fiber, rubber fiber, hemp, manila hemp, sisal hemp, New Zealand hemp, luobuma fiber, coconut, juncus, and wheat straw. In addition, animal fibers such as wool, goat hair, mohair, cashmere, alpaca, angora, camel, vicuna, silk, plumage, down feather, feather, algin fiber, chitin fiber, and casein fiber can be included. Furthermore, mineral fibers such as asbestos can be included.

On the other hand, examples of synthetic fibrous materials include semisynthetic fibers such as rayon, viscose rayon, cupra, acetate, triacetate, oxidized acetate, prommix, chlorinated rubber, hydrochloric acid rubber. In addition to nylon, aramid, polyvinyl alcohol, polyvinyl chloride, and polyvinylidene chloride, synthetic polymeric fibers such as polyester such as polyethylene terephthalate, polyacrylonitrile, acrylic, polyethylene, polypropylene, polystyrene, and polyurethane can be included. Furthermore, metal fibers, carbon fibers, glass fibers, and the like can be used. These fibers can be used alone or in a mixture. Among these, from the viewpoints of the fixability with the oxidizable metal and the reaction accelerator, the flexibility of the steam generating portion 121, the oxygen permeability, the maintenance function of the sheet form, and the manufacturing cost, wood pulp, cotton, polyethylene fiber, polyester fiber are preferably used. In addition, the wood pulp and cotton have a function to support and immobilize solid materials such as iron powder.

As the water absorbent polymer, a hydrophilic polymer having a crosslinked structure capable of absorbing and retaining a liquid more than 20 times its own weight can be included.

As the water absorbent powder, one or more kinds selected from vermiculite, calcium silicate, sawdust, alumina, silica gel, and pulp powder can be included.

In a case where the steam generating portion 121 is in the form of a sheet, it is preferable to use a fibrous material as the water absorbing agent. The reason is that the fibrous material has both the function as a water retaining material and the function of maintaining the sheet form of the steam generating portion 121. As a result, bias of the oxidizable metal is unlikely to occur, and the steam generating portion 121 has a uniform distribution of the heat generation temperature.

In a case where the steam generating portion 121 is a mixture of powders, it is preferable to use a high absorbent polymer, vermiculite, calcium silicate, silica gel, silica based porous material, alumina, wood powder, or the like as the water absorbing agent.

The content of the water absorbing agent is preferably equal to or greater than 0.3 parts by mass, more preferably equal to or greater than 1 part by mass, and still more preferably equal to or greater than 3 parts by mass, with respect to 100 parts by mass of the oxidizable metal. In addition, the content of the water absorbing agent is preferably equal to or less than 100 parts by mass, more preferably equal to or less than 80 parts by mass, and still more preferably equal to or less than 60 parts by mass, with respect to 100 parts by mass of the oxidizable metal.

In addition, the content of the water absorbing agent is preferably equal to or greater than 0.3 parts by mass and equal to or less than 100 parts by mass, more preferably equal to or greater than 1 part by mass and equal to or less than 80 parts by mass, and still more preferably equal to or greater than 3 parts by mass and equal to or less than 60 parts by mass, with respect to 100 parts by mass of the oxidizable metal. In this manner, moisture necessary for sustaining the oxidation reaction can be accumulated in the obtained steam generator 120. In addition, oxygen supply to the steam generating portion 121 is sufficiently obtained, so that the steam generator 120 having high heat generation efficiency is obtained. In addition, since the heat capacity of the steam generator 120 can be suppressed to a small value with respect to the obtained heating value, an increase of heat generation temperature becomes large, an increase in a desired temperature is obtained, and a heat generation reaction can be promoted.

The content of the water absorbing agent is preferably equal to or greater than 4 $g/m^2$ and equal to or less than 290 $g/m^2$, and more preferably equal to or greater than 7 $g/m^2$ and equal to or less than 160 $g/m^2$ in terms of basis weight. In this manner, the thickness of the steam generating portion 121 can be made thin, and the steam generating portion 121 is not bulky and flexible as a product. For example, the thickness of the steam generating portion 121 can be set to equal to or greater than 0.1 mm and equal to or less than 2 mm.

Examples of the electrolyte include sulfates, carbonates, chlorides, or hydroxides of alkali metals, alkaline earth metals, or transition metals. Among these, from the viewpoint of excellent conductivity, chemical stability and manufacturing cost, chlorides of alkali metals, alkaline earth metals, or transition metals are preferably used, and particularly, sodium chloride, potassium chloride, calcium chloride, magnesium chloride, ferrous chloride, ferric chloride are preferably used.

The steam generating portion 121 contains water. The water may be derived from the aqueous electrolyte solution (for example, aqueous solution of an alkali metal, an alkaline earth metal, or the like), or may be one added to the steam generating portion 121 with water alone, and is not particularly limited.

The moisture content in the steam generating portion 121 is preferably equal to or greater than 35 parts by mass and equal to or less than 200 parts by mass with respect to 100 parts by mass of the oxidizable metal. When the moisture content of the steam generating portion 121 is set to equal to or greater than 35 parts by mass with respect to 100 parts by mass of the oxidizable metal, the steam generating portion 121 satisfactorily generates heat and the rise of the heat generation temperature becomes fast (temperature rising time becomes fast). In addition, when the moisture content of the steam generating portion 121 is set to equal to or less than 200 parts by mass with respect to 100 parts by mass of the oxidizable metal, it is possible to ensure the moisture content necessary for the heat generation reaction of the steam generating portion 121 and to satisfactorily maintain the heat generation reaction of the steam generating portion 121.

In this manner, when the moisture content of the steam generating portion 121 is set to equal to or greater than 35 parts by mass and equal to or less than 200 parts by mass with respect to 100 parts by mass of the oxidizable metal, it is possible to obtain the steam generating portion 121 in a satisfactory heat generation state. That is, the moisture content of the steam generating portion 121 affects the heat generation rate. When the moisture content is set to equal to or greater than 35 parts by mass and equal to or less than 200 parts by mass with respect to 100 parts by mass of the oxidizable metal, heat is satisfactorily generated, the rise of the heat generation temperature becomes fast, and the heat generation temperature is maintained.

From the same viewpoint, the moisture content of the steam generating portion 121 is more preferably equal to or greater than 40 parts by mass, and still more preferably equal to or greater than 50 parts by mass with respect to 100 parts by mass of the oxidizable metal. In addition, the moisture content of the steam generating portion 121 is preferably equal to or less than 200 parts by mass, more preferably equal to or less than 150 parts by mass, still more preferably equal to or less than 100 parts by mass, and even more preferably equal to or less than 80 parts by mass with respect to 100 parts by mass of the oxidizable metal.

In addition, the moisture content of the steam generating portion 121 is more preferably equal to or greater than 40 parts by mass and equal to or less than 150 parts by mass, still more preferably equal to or greater than 50 parts by mass and equal to or less than 100 parts by mass, and even more preferably equal to or greater than 50 parts by mass and equal to or less than 80 parts by mass with respect to 100 parts by mass of the oxidizable metal.

In addition to the above-described components, the steam generating portion 121 may contain a thickener, a surfactant, a chemical, a flocculant, a colorant, a paper strength enhancer, a pH adjuster (for example, tripotassium phosphate), a bulking agent, and the like.

As the thickener, the thickener absorbs moisture to increase consistency, or a substance imparting thixotropy can be used, and one or more kinds of mixtures selected from polysaccharide based thickeners such as alginate such as sodium alginate, gum arabic, gum tragacanth, locust bean gum, guar gum, carrageenan, agar, xanthan gum; starch based thickeners such as dextrin, pregelatinized starch, processing starches; cellulose derivative type thickeners such as carboxymethyl cellulose, ethyl cellulose acetate, hydroxyethyl cellulose, hydroxymethyl cellulose, or hydroxypropyl cellulose; thickeners such as polyvinyl alcohol (PVA); metal soap based thickeners such as stearate; mineral based thickeners such as bentonite, and the like, can be used. Among these, a polysaccharide based thickener is preferable, and xanthan gum is preferable from the viewpoint of maintaining the moisture content constant in the steam generating portion 121.

In a case where the steam generating portion 121 is a coated sheet, the content of the thickener is preferably equal to or greater than 0.1 parts by mass, and more preferably equal to or greater than 0.2 parts by mass with respect to 100 parts by mass of the oxidizable metal from the viewpoint of ease of coating. In addition, the content of the thickener is preferably equal to or less than 5 parts by mass, and more preferably equal to or less than 4 parts by mass with respect to 100 parts by mass of the oxidizable metal. The content of the thickener is preferably equal to or greater than 0.1 parts by mass and equal to or less than 5 parts by mass, and more preferably equal to or greater than 0.2 parts by mass and equal to or less than 4 parts by mass with respect to 100 parts by mass of the oxidizable metal.

In addition, in a case where the steam generating portion 121 is in the form of a sheet, it is preferable that a large number of holes and/or incisions are formed. As a result, even if the sheet-like steam generating portion 121 is thin, high heat generation characteristics can be sufficiently obtained and a desired steam discharge characteristic can be obtained. It is preferable that the area of the hole is 0.01 to 10 $mm^2$, and particularly 0.1 to 8 $mm^2$ since sufficient heat generation characteristics can be obtained. For the same reason, it is preferable that the holes are formed at 0.1 to 20 holes/$cm^2$, and particularly 1 to 15 holes/$cm^2$ in the sheet-like steam generating portion 121. Examples of the shape of the hole include a circle, a rectangle, a polygon, an ellipse, an oval, or a combination of two or more types of these. On the other hand, in a case of forming incisions, the length thereof is preferably 1 to 50 mm, and particularly preferably 5 to 30 mm.

The steam generating portion 121 is accommodated in the bag body 122 provided with a first sheet 122A and a second sheet 122B of the steam generator 120. That is, the steam generator 120 is configured to include the first sheet 122A and the second sheet 122B, and the peripheral edge portions of the first sheet 122A and the second sheet 122B are preferably hermetically bonded to form the bag body 122. Regions other than the peripheral edge portions of the first sheet 122A and the second sheet 122B are non-bonded regions, and the steam generating portion 121 is disposed in the non-bonded region.

In the present embodiment, the following configuration is adopted for the steam generating portion 121.

That is, in the steam generator 120, the first sheet 122A is disposed on the surface of the steam generating portion 121 on the side of the wearer, and the degree of air permeability of the first sheet 122A is equal to or less than 7,000 sec/100 ml. The second sheet 122B is disposed on the surface of the steam generating portion 121 opposite to the surface on the side of the wearer, and the degree of air permeability of the second sheet 122B exceeds 8,000 sec/100 ml.

These configurations will be described later in detail.

In the present embodiment, the surface of the steam generator 120 located on the side of the wearer is the first sheet 122A.

Here, the degree of air permeability of the first sheet 122A is equal to or less than 7,000 sec/100 ml. From the viewpoint of holding the space surrounded by the steam generator 120 and the depression of the face between the nose portion and the cheek portion, ensuring air permeability, and easily discharging a large amount of steam from the steam generator 120 to the outside of the bag body 122, the degree of air permeability of the first sheet 122A is preferably equal to or less than 5,000 sec/100 ml, more preferably equal to or less than 2,500 sec/100 ml, still more preferably equal to or less than 1,000 sec/100 ml, still more preferably equal to or less than 600 sec/100 ml, still more preferably equal to or less than 10 sec/100 ml, still more preferably equal to or less than 5 sec/100 ml, and even more preferably equal to or less than 0 sec/100 ml.

As the first sheet 122A having such degree of air permeability, for example, it is preferable to use a porous sheet made of a synthetic resin with moisture permeability and without water permeability. Specifically, a film obtained by stretching and containing calcium carbonate or the like in polyethylene can be used. In a case of using such a porous sheet, various fiber sheets such as one or more kinds of nonwoven fabrics selected from a needle-punched nonwoven fabric, an air-through nonwoven fabric, and a spunbonded nonwoven fabric on the outer surface of the porous sheet may be laminated to enhance the texture of the first sheet 122A.

In addition, when the above degree of air permeability is satisfied, a portion of the first sheet 122A may be a non-air permeable sheet not having air permeability.

A portion of the second sheet 122B may be an air permeable sheet having air permeability or a non-air permeable sheet not having air permeability, but a sheet having low air permeability is adopted as a whole. Specifically, the condition that the degree of air permeability of the second sheet 122B exceeds 8,000 sec/100 ml is adopted, but from the viewpoint of effectively and stably heating and humidifying the inside of the mask body portion 101, it is preferable to use a non-air permeable sheet.

When the above degree of air permeability is satisfied, the second sheet 122B can be obtained by laminating various fiber sheets such as one or more kinds of nonwoven fabrics selected from a needle-punched nonwoven fabric, an air-through nonwoven fabric, and a spunbonded nonwoven fabric on a film having the single layer or multilayer synthetic resin, or an outer surface of film having the single layer or multilayer synthetic resin depending on the application, and the texture of the second sheet 122B can be enhanced. Specifically, a two-layer film including a polyethylene film and a polyethylene terephthalate film, a laminate film including a polyethylene film and a nonwoven fabric, a laminate film including a polyethylene film and a pulp sheet, and the like are used, and a laminate film including a polyethylene film and a pulp sheet is still more preferred.

When the value of the above degree of air permeability is satisfied, the second sheet 122B can use the same material as the first sheet 122A, or can use a different material.

In addition, the air permeability of the second sheet 122B is preferably equal to or greater than 10,000 sec/100 ml, more preferably equal to or greater than 30,000 sec/100 ml, and still more preferably equal to or greater than 80,000 sec/100 ml. When the air permeability of the second sheet 122B is set in this manner, it is possible to efficiently discharge the steam generated in the steam generating portion 121 from the side of the first sheet 122A, and to suppress expansion of the steam generator 120.

In particular, from the viewpoint of making the oxidation reaction of the oxidizable metal favorable and making it easy to generate a large amount of steam from the side of the first sheet 122A, it is even more preferred that the degree of air permeability of the first sheet 122A is equal to or less than 2,500 sec/100 ml and the degree of air permeability of the second sheet 122B be equal to or greater than 80,000 sec/100 ml.

In this case, on the surface opposite to the surface of the steam generating portion 121 located on the side of the wearer, that is, between the steam generating portion 121 and the outermost layer on the side opposite to the wearer of the steam generator 120, non-air permeable or air impermeable sheet, more preferably non-air permeable sheet, are disposed. As a result, the steam generated by the steam generating portion 121 can be prevented from leaking to the outside of the mask 110, and the steam can be applied inside the mask 110, that is, the side of the wearer.

An example of a method for manufacturing the steam generating portion 121 will be described below.

In a case where the steam generating portion 121 is in the form of, for example, a sheet, for example, a wet paper making method described in Japanese Unexamined Patent Publication NO. 2003-102761 according to the previous application by the present applicant, or an extrusion method using a die coater can be used. In this case, first, a molded sheet containing an oxidizable metal, a water absorbing agent, and a reaction accelerator is formed by a wet paper making method, and by adding an electrolytic aqueous solution to this molded sheet, a sheet-like steam generating portion 121 is obtained. The obtained sheet-like steam generating portion 121 may be used as one sheet, or a plurality of sheets may be stacked and used. Alternatively, one steam generating portion 121 may be folded, and a plurality of folded steam generating portions 121 may be stacked and used.

In a case where the steam generating portion 121 is configured to include powder, the constituent materials are homogeneously mixed to obtain a powder steam generating portion 121. More specifically, firstly, a water absorbing agent such as a superabsorbent polymer and an oxidizable metal are homogeneously mixed, an aqueous electrolytic solution is added thereto, and the oxidizable metal is attached to the surface of the water absorbing agent. Thereafter, a reaction accelerator or the like as the remaining materials is added, so that the steam generating portion 121 can be prepared. The steam generating portion 121 is prepared in this manner, so that the rise time of the oxidation reaction becomes earlier and the evaporation amount of steam per unit time easily reaches the maximum value.

In addition, in a case where the steam generating portion 121 includes a coated sheet, for example, according to the method described in Japanese Unexamined patent publication NO. 2013-146554 according to the previous application by the present applicant, the steam generating portion 121 may be one obtained by applying a heating powder aqueous dispersion to a water retaining sheet and cutting a continuous long object of heat generation material provided with a heat generating layer and a water retaining sheet into an arbitrary size. The steam generating portion 121 may be one sheet or may be accommodated in a multilayer state in which a plurality of sheets are stacked.

Here, the configuration of the steam generator 120 in a case where the steam generating portion 121 includes the coated sheet will be described below.

As shown in FIG. 9, the steam generating portion 121 has a steam generating layer 121A between a base material layer 121B and a water retaining sheet 121C. The steam generating layer 121A and the water retaining sheet 121C are in direct contact with each other. The steam generator 120 is provided with a steam generating portion 121 in the bag body 122 having the first sheet 122A and the second sheet 122B so that the water retaining sheet 121C, that is, the side of the first sheet 122A is positioned on the skin side of the wearer, and the base material layer 121B is disposed on the second sheet 122B side. As a result, the steam from the steam generating portion 121 can be efficiently discharged from the first sheet 122A.

The steam generating layer 121A may be provided on one side of the water retaining sheet 121C, or may be provided in a form interposed between the water retaining sheet 121C and the base material layer 121B. FIG. 9 shows an example in which the steam generating layer 121A is provided so as to be interposed between the water retaining sheet 121C and the base material layer 121B.

The water retaining sheet 121C contains water. For example, the content of water can be equal to or greater than 10% by mass and equal to or less than 45% by mass of the maximum amount of water absorption of the water retaining sheet 121C.

The maximum amount of water absorption of the water retaining sheet 121C can be calculated as follows.

After measuring the mass ($W_0$) of the water retaining sheet 121C cut to a size of 25 cm², the water retaining sheet 121C is immersed in a 5% by mass sodium chloride aqueous solution for 5 minutes. The sheet is taken out with tweezers, and is hung and left in air for 1 minute to drip and drop a moisture that cannot be held, drop it. Thereafter, the mass ($W_1$) is measured, and the maximum amount of water absorption ($W_{max}$) is calculated from the following formula.

$$W_{max} = W_1 - W_0$$

In addition, the moisture content contained in the water retaining sheet 121C is preferably 50 to 350 g/m², and more preferably 180 to 260 g/m² in terms of basis weight. Since the moisture content contained in the water retaining sheet 121C is a steam generation source, the moisture content contained in the water retaining sheet 121C is set to preferably equal to or greater than 50 g/m² in terms of basis weight, so that a favorable steam generation amount can be ensured. In addition, the water retaining sheet 121C generates the air permeation resistance due to water absorption (air permeability decreases as compared with drying, due to water absorption swelling,). Therefore, the moisture content is set to preferably equal to or less than 350 g/m² in terms of basis weight, so that it is easy to discharge the steam from the water retaining sheet 121C, and the air permeability to the steam generating layer 121A is sufficiently ensured. Therefore, the steam generator 120 having sufficient oxygen supply and high heat generation efficiency can be obtained.

In addition, the degree of air permeability of the water retaining sheet 121C is preferably equal to or less than 500 sec/100 ml in the degree of air permeability in a state of containing moisture. When the air permeability and ease of passing steam are considered, it is more preferably equal to or less than 300 sec/100 ml, and still more preferably equal to or less than 50 sec/100 ml.

For example, a lower limit value of the degree of air permeability is 1 sec/100 ml in a state containing moisture (that is, moisture content is equal to or greater than 15% by mass and equal to or less than 30% by mass of the maximum amount of water absorption of the water retaining sheet 121C).

Here, as the water retaining sheet 121C, a sheet material capable of absorbing and retaining moisture and having flexibility is used. Examples of such materials include a fiber sheet such as paper, nonwoven fabric, woven fabric, knitted fabric or the like made from fibers. In addition, a porous body such as sponge is included. Examples of the above fibers include fibers based on natural fibers such as vegetable fibers and animal fibers, and fibers based on chemical fibers. Examples of vegetable fibers include one or more kinds selected from cotton, kapok, wood pulp, non-wood pulp, peanut protein fiber, corn protein fiber, soy protein fiber, mannan fiber, rubber fiber, hemp, manila hemp, sisal hemp, New Zealand hemp, luobuma fiber, coconut, juncus, and wheat straw. Examples of animal fibers include one or more kinds selected from wool, goat hair, mohair, cashmere, alpaca, angora, camel, vicuna, silk, plumage, down feather, feather, algin fiber, chitin fiber, and casein fiber. As the chemical fiber, for example, one or more kinds selected from rayon, acetate, cellulose can be used.

Among these, as the water retaining sheet 121C, a sheet containing the fiber material including the above-described fibers and the water absorbent polymer is preferable.

As the water absorbent polymer, it is preferable to use a hydrogel material capable of absorbing and retaining a liquid more than 20 times its own weight and capable of gelling because the water content contained in the water retaining sheet 121C can be maintained at 15% to 30% by mass of the maximum amount of water absorption of the water retaining sheet 121C.

Examples of the shape of the particles of the water absorbent polymer include a spherical shape, a lumpy shape, a grape-like shape, a fibrous shape, and the like.

In addition, the particle diameter of the water absorbent polymer particles is preferably equal to or greater than 1 μm, and more preferably equal to or greater than 10 μm, from the viewpoint of ease of handling at the time of manufacturing. In addition, the particle diameter of the water absorbent polymer particles is preferably equal to or less than 1,000 μm, and more preferably equal to or less than 500 μm, from the viewpoint of water absorption speed.

In addition, the particle diameter of the water absorbent polymer particles is preferably equal to or greater than 1 μm and equal to or less than 1,000 μm, and more preferably equal to or greater than 10 μm and equal to or less than 500 μm.

The particle diameter of the water absorbent polymer particles is measured by a dynamic light scattering method, a laser diffraction method, or the like.

Specific examples of the water absorbent polymers include one or more kinds selected from starch, crosslinked carboxyl methylated cellulose, a polymer or copolymer of acrylic acid or an alkali metal salt of acrylic acid, and polyacrylic acid, a salt thereof, and a polyacrylate graft polymer. Among these, it is preferable to use a polymer or copolymer of acrylic acid or an alkali metal salt of acrylic acid, and polyacrylic acid, salt thereof, and polyacrylate graft polymer.

The base material layer 121B is disposed on the surface of the steam generating layer 121A opposite to the water retaining sheet 121C. The base material layer 121B is in direct contact with the steam generating layer 121A and covers the steam generating layer 121A. The base material layer 121B is preferably a non-air permeable or air impermeable sheet, and for example, a resin sheet is preferably used. By using the non-air permeable or air impermeable sheet (equal to or greater than 50,000 sec/100 ml, and preferably equal to or greater than 80,000 sec/100 ml), it is possible not only to more reliably discharge the steam from the water retaining sheet 121C side, but also to prevent vaporization heat from being deprived from the base material layer 121B side.

Examples of the base material layers 121B include a synthetic resin film, a polyethylene film, a polyethylene terephthalate film, and the like.

In a case where the water retaining sheet 121C is formed on the steam generating layer 121A and the base material layer 121B is not provided, there is a possibility that the steam generating portion 121 is in direct contact with the second sheet 122B. Therefore, it is preferable that the second sheet 122B is a sheet having water resistance.

The steam generation amount of the steam generator 120 of the present embodiment is preferably equal to or greater than 30 mg/cell·10 min, more preferably equal to or greater than 50 mg/cell·10 min, still more preferably equal to or greater than 150 mg/cell·10 min, still more preferably equal to or greater than 250 mg/cell·10 min, and even more preferably equal to or greater than 300 mg/cell·10 min, as a whole of the steam generator 120 from the viewpoint of imparting an appropriate steam feeling to the mask wearer.

In addition, the steam generation amount of the steam generator 120 of the present embodiment is preferably equal to or less than 1,200 mg/cell·10 min, more preferably equal to or less than 1,000 mg/cell·10 min, still more preferably equal to or less than 800 mg/cell·10 min, still more preferably equal to or less than 700 mg/cell·10 min, and even more preferably equal to or less than 500 mg/cell·10 min, as a whole of the steam generator 120 from the viewpoint of suppressing dew condensation in the mask.

In addition, the steam generation amount of the steam generator 120 of the present embodiment is preferably equal to or greater than 30 mg/cell·10 min and equal to or less than 1,200 mg/cell·10 min, more preferably equal to or greater than 50 mg/cell·10 min and equal to or less than 1,000 mg/cell·10 min, still more preferably equal to or greater than 150 mg/cell·10 min and equal to or less than 800 mg/cell·10 min, still more preferably equal to or greater than 250 mg/cell·10 min and equal to or less than 700 mg/cell·10 min, and even more preferably equal to or greater than 300 mg/cell·10 min and equal to or less than 500 mg/cell·10 min, as a whole of the steam generator 120.

In addition, the steam generation amount per unit area of the steam generator 120 of the present embodiment is preferably equal to or greater than 1 mg/cm$^2$·10 min, more preferably equal to or greater than 1.5 mg/cm$^2$·10 min, still more preferably equal to or greater than 5 mg/cm$^2$·10 min, still more preferably equal to or greater than 7 mg/cm$^2$·10 min, and even more preferably equal to or greater than 9 mg/cm$^2$·10 min, as a whole of the steam generator 120 from the viewpoint of imparting an appropriate steam feeling to the mask wearer.

In addition, the steam generation amount per unit area of the steam generator 120 of the present embodiment is preferably equal to or less than 20 mg/cm$^2$·10 min, more preferably equal to or less than 18 mg/cm$^2$·10 min, and still more preferably equal to or less than 15 mg/cm$^2$·10 min, as a whole of the steam generator 120 from the viewpoint of suppressing dew condensation in the mask.

In addition, the steam generation amount per unit area of the steam generator 120 of the present embodiment is preferably equal to or greater than 1 mg/cm$^2$·10 min and equal to or less than 20 mg/cm$^2$·10 min, more preferably equal to or greater than 1.5 mg/cm$^2$·10 min and equal to or less than 18 mg/cm$^2$·10 min, still more preferably equal to or greater than 5 mg/cm$^2$·10 min and equal to or less than 15 mg/cm$^2$·10 min, still more preferably equal to or greater than 7 mg/cm$^2$·10 min and equal to or less than 15 mg/cm$^2$·10 min, and even more preferably equal to or greater than 9 mg/cm²·10 min and equal to or less than 15 mg/cm²·10 min, as a whole of the steam generator 120.

[Measurement Method for Steam Generation Amount]

Figure 11:
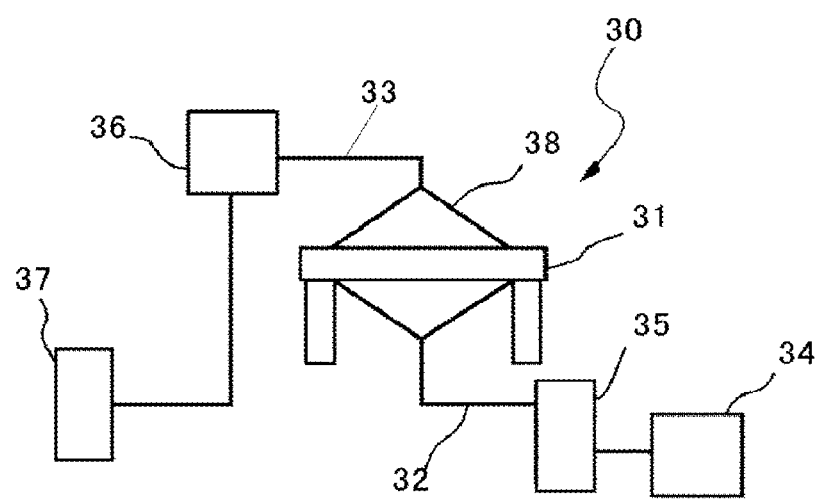
FIG. 11 is a schematic diagram showing an apparatus which measures the steam generation amount.

Here, the steam generation amount of the steam generator 120 or the steam heating mask 100 is a numerical value measured using the apparatus 30 shown in FIG. 11 as follows. The apparatus 30 shown in FIG. 11 includes an aluminum measurement chamber 31 (volume 2.1 L), an inflow path 32 through which dehumidified air (humidity less than 2% and flow rate 2.1 L/min) flows into the lower portion of the measurement chamber 31, an outflow path 33 through which air flows out from the upper portion of the measurement chamber 31, an inlet thermo-hygrometer 34 and an inlet flow meter 35 provided in the inflow path 32, an outlet thermo-hygrometer 36 and an outlet flow meter 37 provided in the outflow path 33, and a thermometer (thermistor) 38 provided in the measurement chamber 31. As the thermometer 38, one having a temperature resolution of approximately 0.01° C. is used.

In the measurement of the surface temperature of the surface positioned on the skin side of the steam generator 120 or the steam heating mask 100, the steam generator 120 is taken out from the oxygen blocking bag, placed on the measurement chamber 31 with the surface positioned on the skin side of the steam generator 120 or the steam heating mask 100, that is, the steam discharge surface facing upward, and the thermometer 38 with metal ball (4.5 g) attached is placed thereon for measurement, at measurement environment temperature 30° C. (30±1° C.). In addition, in this state, dehumidified air flows from the lower portion, a difference between the absolute humidity before and after the air flows into the measurement chamber 31 is obtained from the temperature and the humidity measured by the inlet thermo-hygrometer 34 and the outlet thermo-hygrometer 36. Furthermore, the amount of steam discharged by the steam generator 120 or the steam heating mask 100 is calculated from the flow rate measured by the inlet flow meter 35 and the outlet flow meter 37. In the present specification, the steam generation amount refers to the total amount measured up to 10 minutes after the point when the steam generator 120 is taken out from the oxygen blocking bag as a starting point.

In addition, the steam generation amount of the steam heating mask 100 of the present embodiment is preferably equal to or greater than 60 mg/10 min, more preferably equal to or greater than 100 mg/10 min, still more preferably equal to or greater than 300 mg/10 min, still more preferably equal to or greater than 500 mg/10 min, and even more preferably equal to or greater than 600 mg/10 min, from the viewpoint of imparting an appropriate steam feeling to the mask wearer.

In addition, the steam generation amount of the steam heating mask 100 of the present embodiment is preferably equal to or less than 2,000 mg/10 min, more preferably equal to or less than 1,400 mg/10 min, and still more preferably equal to or less than 1,000 mg/10 min, from the viewpoint of suppressing dew condensation in the mask.

In addition, the steam generation amount of the steam heating mask 100 of the present embodiment is preferably equal to or greater than 60 mg/10 min and equal to or less than 2,000 mg/10 min, more preferably equal to or greater than 100 mg/10 min and equal to or less than 1,400 mg/10 min, still more preferably equal to or greater than 300 mg/10 min and equal to or less than 1,000 mg/10 min, still more preferably equal to or greater than 500 mg/10 min and equal to or less than 1,000 mg/10 min, and even more preferably equal to or greater than 600 mg/10 min and equal to or less than 1,000 mg/10 min.

Next, the effect of the steam heating mask 100 will be described.

The steam heating mask 100 is a combination of the mask 110 and the steam generator 120 described above, the surface of the steam generator 120 positioned on the side of the wearer is covered with a sheet having a degree of air permeability of equal to or less than 7,000 sec/100 ml, and a sheet having a degree of air permeability of greater than 8,000 sec/100 ml is disposed on the surface of the steam generator 120 opposite to the surface positioned on the side of the wearer.

That is, the degree of air permeability of the first sheet 122A is set to equal to or less than 7,000 sec/100 ml, and the degree of air permeability of the second sheet 122B is set to greater than 8,000 sec/100 ml, so that the steam generated by the steam generating portion 121 can be prevented from leaking to the outside of the mask 110, and the steam can be applied inside the mask 110, that is, the side of the wearer.

The proportion of the area occupied by the steam generator 120 is set to equal to or greater than 30% and equal to or less than 80%, with respect to the area of the entire surface of the mask body portion 101 on the side of the wearer, so that the absolute humidity inside the mask 110 can be enhanced, without imparting the feeling of stuffiness to the wearer.

By the synergistic effect of these effects, it is possible to breathe easily, positively generate steam heated in the mask, and increase the absolute humidity in the mask. It is possible to improve comfort by heating and humidifying and a moist feeling of mucous membranes of a throat and nose. In addition, due to such an effect, it is possible to ease breathing by reducing discomfort due to nasal obstruction and the like, and to enhance the function of transporting mucosal pilus. Therefore, an effect of promoting the function of discharging foreign matter can be obtained.

The steam heating mask 100 is used, for example, as follows.

That is, in a case where the mask 110 and the steam generator 120 are separated, the steam heating mask 100 opens the oxygen blocking bag, takes out the steam generator 120, and fixes the steam generator 120 at a predetermined position of the mask 110. The mask 110 is attached so that the ear hook portion 102 hangs on the ear of the wearer and the mouth and the nose of the wearer are covered with the mask body portion 101.

In addition, in a case where the steam generator 120 is sealed in the accommodation body 104 of the mask 110, the steam generator 120 is normally sealed in the oxygen blocking bag as a whole of the steam heating mask 100. As a method of use in this case, after breaking the oxygen blocking bag, the steam heating mask 100 is taken out, each ear hook portion 102 is hung on the ear of the wearer, and the mask body portion 101 is attached so as to cover the mouth and the nose of the wearer.

The steam generator 120 reacts with oxygen in the air, generates heat, and generates the steam. The steam generated in the mask 110 is aspirated from the mouth and the nose of the wearer, a feeling of dryness of the throat and nose due to a low temperature and low humidity environment is relaxed, and a discomfort due to nasal obstruction and the like is reduced, so that a relaxation effect is obtained and a comfort can be obtained. In addition, a feeling of sleep is induced. Furthermore, since the mucous membranes of the nasal cavity are heated and humidified, the function of discharging foreign matter is enhanced and a preventive effect such as a cold can be expected.

In addition, since the corner layer is thin, the lip portion is sensitive to temperature and the heat generated by the steam generator 120 touches the lip portion, so that the lip portion is likely to feel sensitive to hot feeling, whereas by heating the lateral portion of the nose, such problems can be suppressed.

The maximum absolute humidity in the mask during use of the steam heating mask 100 in the present embodiment is preferably equal to or greater than 12 g/m$^3$, more preferably equal to or greater than 13 g/m$^3$, still more preferably equal to or greater than 15 g/m$^3$, still more preferably equal to or greater than 20 g/m$^3$, and even more preferably equal to or greater than 25 g/m$^3$, from the viewpoint of bringing comfortable steam to the wearer.

In addition, the maximum absolute humidity in the mask during use of the steam heating mask 100 is preferably equal to or less than 50 g/m$^3$, more preferably equal to or less than 45 g/m$^3$, still more preferably equal to or less than 40 g/m$^3$, and even more preferably equal to or less than 35 g/m$^3$, from the viewpoint of preventing dew condensation in the mask.

In addition, the maximum absolute humidity in the mask during use of the steam heating mask 100 is preferably equal to or greater than 12 g/m$^3$ and equal to or less than 50 g/m$^3$, more preferably equal to or greater than 13 g/m$^3$ and equal to or less than 45 g/m$^3$, still more preferably equal to or greater than 15 g/m$^3$ and equal to or less than 40 g/m$^3$, still more preferably equal to or greater than 20 g/m$^3$ and equal to or less than 35 g/m$^3$, and even more preferably equal to or greater than 25 g/m$^3$ and equal to or less than 35 g/m$^3$.

In addition, the average absolute humidity in the mask during use of the steam heating mask 100 in the present embodiment is preferably equal to or greater than 11.7 g/m$^3$, more preferably equal to or greater than 12 g/m$^3$, still more preferably equal to or greater than 13 g/m$^3$, still more preferably equal to or greater than 15 g/m$^3$, and even more preferably equal to or greater than 19 g/m$^3$, from the viewpoint of bringing comfortable steam to the wearer.

In addition, the average absolute humidity in the mask during use of the steam heating mask 100 is preferably equal to or less than 35 g/m$^3$, more preferably equal to or less than 30 g/m$^3$, and still more preferably equal to or less than 25 g/m$^3$, from the viewpoint of preventing dew condensation in the mask.

In addition, the average absolute humidity in the mask during use of the steam heating mask 100 is preferably equal to or greater than 11.7 g/m$^3$ and equal to or less than 35 g/m$^3$, more preferably equal to or greater than 12 g/m$^3$ and equal to or less than 30 g/m$^3$, still more preferably equal to or greater than 13 g/m$^3$ and equal to or less than 25 g/m$^3$, still more preferably equal to or greater than 15 g/m$^3$ and equal to or less than 25 g/m$^3$, and even more preferably equal to or greater than 19 g/m$^3$ and equal to or less than 25 g/m$^3$, from the viewpoint of bringing comfortable steam to the wearer.

The absolute humidity at the time of using the steam heating mask 100 can be measured as follows.

[Measurement Condition for Absolute Humidity]

At an environment of 20° C. and 60% RH, a temperature and humidity sensor (SHT 71 manufactured by Sensirion Co., Ltd.) is attached to the lower portion of the nose of the head model mannequin prepared using male human head data (average of 52 Japanese adult males) of Digital Human Technology Co., Ltd., and air is inhaled at a frequency of 500 ml each time and 15 times per minute from the nose portion of the head model, using a ventilator ((HARVARD APPARATUS DUAL PHASE CONTROL RESPIRATOR (manufactured by HARVARD APPARATUS Co., Ltd.)) and simulating a human respiratory rhythm. In this state, the steam heating mask 100 is attached to the mannequin, the change in temperature and humidity is measured and recorded. As the recorder, for example, EK-H4 manufactured by Sensirion Co., Ltd. is used. The absolute humidity is calculated from the temperature and relative humidity, and the maximum absolute humidity and the average absolute humidity for 10 minutes are obtained.

Second Embodiment

In the first embodiment, the example in which the degree of air permeability of the first sheet is equal to or less than 7,000 sec/100 ml and the degree of air permeability of the second sheet is greater than 8,000 sec/100 ml is described, and in the second embodiment, the degrees of air permeability of the first sheet and the second sheet is set as follows.

That is, in the present embodiment, the degree of air permeability of the second sheet is equal to or greater than 250 sec/100 ml and 8,000 sec/100 ml or less, and the degree of air permeability of the first sheet is equal to or less than 20% of the degree of air permeability of the second sheet.

Hereinafter, the present embodiment will be described.

Descriptions of similar configurations and effects of the first embodiment will appropriately not be repeated.

In the present embodiment, a portion of the second sheet 122B may be an air permeable sheet which has the air permeability, or a non-air permeable sheet which has not the air permeability, but as a whole, a condition of equal to or greater than 250 sec/100 ml and equal to or less than 8,000 sec/100 ml is adopted as the degree of air permeability of the second sheet 122B.

From the viewpoint of preventing abnormal heat generation of the steam generator, and from the viewpoint of appropriately distributing the steam generated from the steam generating portion 121 and sufficiently applying the steam to the side of the wearer, the degree of air permeability of the second sheet 122B is preferably equal to or greater than 4,000 sec/100 ml and equal to or less than 7,500 sec/100 ml, and more preferably equal to or greater than 5,000 seconds/100 mL and equal to or less than 7,000 seconds/100 mL.

When the above degree of air permeability is satisfied, the second sheet 122B can be obtained by laminating various fiber sheets such as one or more kinds of nonwoven fabrics selected from a needle-punched nonwoven fabric, an airthrough nonwoven fabric, and a spunbonded nonwoven fabric on a film having the single layer or multilayer synthetic resin, or an outer surface of film having the single layer or multilayer synthetic resin depending on the application, and the texture of the second sheet 122B can be enhanced. Specifically, a two-layer film including a polyethylene film and a polyethylene terephthalate film, a laminate film including a polyethylene film and a nonwoven fabric, a laminate film including a polyethylene film and a pulp sheet, and the like are used, and a laminate film including a polyethylene film and a pulp sheet is still more preferred.

In the present embodiment, the degree of air permeability of the first sheet 122A positioned on the surface of the steam generator 120 on the side of the wearer is equal to or less than 20% of the degree of air permeability of the second sheet 122B.

From the viewpoint of appropriately distributing the steam generated from the steam generating portion 121 and sufficiently applying the steam to the side of the wearer, and from the viewpoint of suppressing the swelling of the steam generator and preventing the feeling of stuffiness when wearing the steam heating mask, the degree of air permeability of the first sheet 122A is preferably equal to or less than 10%, more preferably equal to or less than 5%, still more preferably equal to or less than 3%, still more preferably equal to or less than 1%, and even more preferably 0% of the degree of air permeability of the second sheet 122B.

Although the degree of air permeability of the first sheet 122A can be appropriately selected from those satisfying the condition that it is equal to or less than 20% of the degree of air permeability of the second sheet 122B, from the viewpoint of appropriately distributing the steam generated from the steam generating portion 121 and sufficiently applying the steam to the side of the wearer, and from the viewpoint of suppressing the swelling of the steam generator and preventing the feeling of stuffiness when wearing the steam heating mask, more specifically, it is preferably equal to or less than 1,600 sec/100 ml, more preferably equal to or less than 1,000 sec/100 ml, still more preferably equal to or less than 250 sec/100 ml, still more preferably equal to or less than 10 sec/100 ml, still more preferably equal to or less than 5 sec/100 ml, and even more preferably 0 sec/100 ml of the degree of air permeability of the second sheet 122B.

As the first sheet 122A having such degree of air permeability, for example, it is preferable to use a porous sheet made of a synthetic resin having moisture permeability but not having water permeability. Specifically, a film obtained by containing and stretching calcium carbonate or the like in polyethylene can be used. In a case of using such a porous sheet, various fiber sheets such as one or more kinds of nonwoven fabrics selected from a needle-punched nonwoven fabric, an air-through nonwoven fabric, and a spunbonded nonwoven fabric may be laminated on the outer surface of the porous sheet, and the texture of the first sheet 122A may be enhanced.

In addition, when the above degree of air permeability is satisfied, a portion of the first sheet 122A may be a non-air permeable sheet not having the air permeability.

Next, effects of the steam heating mask 100 of the present embodiment will be described.

That is, in the steam heating mask 100 of this embodiment, the degree of air permeability of second sheet 122B is set to equal to or less than 8,000 sec/100 ml, and the degree of air permeability of the first sheet 122A is set to equal to or less than 20% of the degree of air permeability of the second sheet 122B, so that the steam generated by the steam generating portion 121 can be prevented from leaking to the outside of the mask 110, and the steam can be applied inside the mask 110, that is, the side of the wearer.

The proportion of the area occupied by the steam generator 120 is set to equal to or greater than 30% and equal to or less than 80%, with respect to the area of the entire surface of the mask body portion 101 on the side of the wearer, so that the absolute humidity inside the mask 110 can be enhanced, without imparting the feeling of stuffiness to the wearer.

By the synergistic effect of these effects, it is possible to breathe easily, positively generate steam heated in the mask, and increase the absolute humidity in the mask. It is possible to improve comfort by heating and humidifying and a moist feeling of mucous membranes of a throat and nose. In addition, due to such an effect, it is possible to ease breathing by reducing discomfort due to nasal obstruction and the like, and to enhance the function of transporting mucosal pilus.

Therefore, an effect of promoting the function of discharging foreign matter can be obtained.

Third Embodiment

In the first embodiment, an example in which the accommodation body 104 is used as the fixing means is described, and in the third embodiment, an example in which an adhesive is used as the fixing means will be described. Descriptions of similar configurations and effects of the first embodiment and the second embodiment will appropriately not be repeated.

Figure 7:
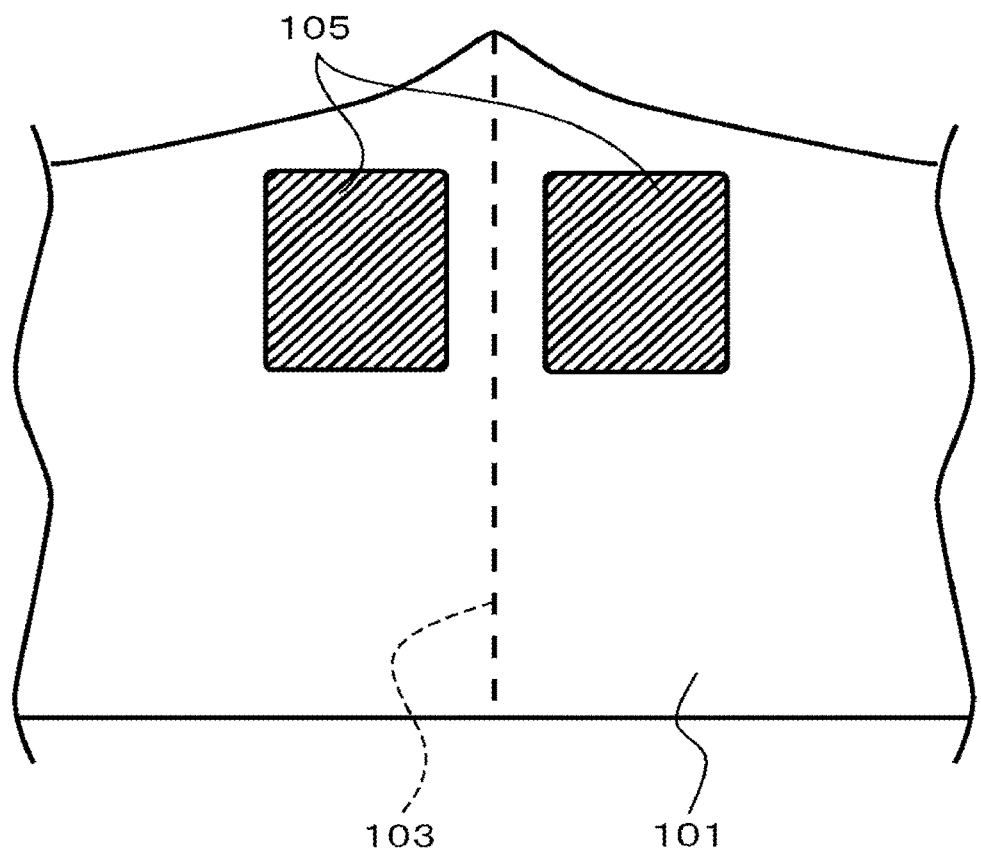
FIG. 7 is a partial plan view of a mask seen from a surface on a side of a wearer before attaching a steam generator to the mask according to a third embodiment.
Figure 8:
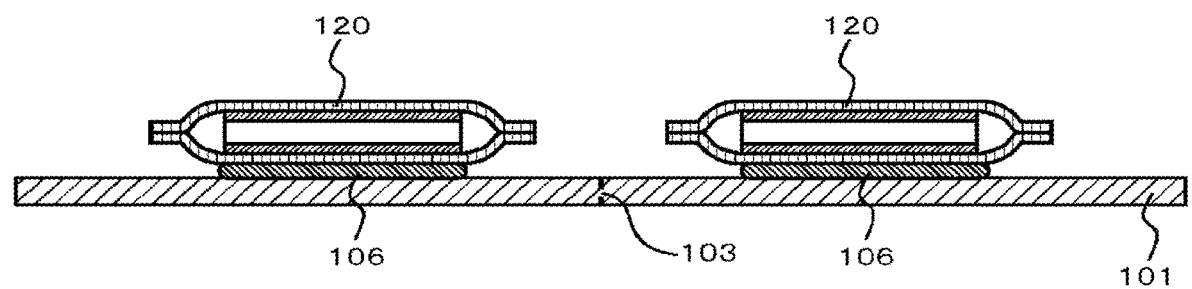
FIG. 8 is a cross-sectional view of a portion of a mask seen from an upper surface (eye side of a wearer) according to the third embodiment.

FIG. 7 is a partial plan view of a mask seen from a surface on a side of a wearer before attaching a steam generator to the mask according to a third embodiment. FIG. 8 is a cross-sectional view of a portion of a mask seen from an upper surface (eye side of a wearer) according to the third embodiment.

[Mask]

The mask body portion 101 can use materials similar to those of the first embodiment and the second embodiment.

In the present embodiment, as shown in FIG. 7, it is preferable that a marking region 105 is formed on the surface of the mask body portion 101 on the side of the wearer, so that the position where the steam generator 120 is to be attached can be known. As shown in FIG. 8, the steam generator 120 is fixed to the mask body portion 101 on the marking region 105 via an adhesive 106. In the marking area 105, the color in the region may be changed by printing or embossing may be performed. In addition, the marking region 105 may be provided with lines such as a solid line and a dotted line around the marking region 105.

In addition, from the viewpoint of improving the feeling of wearing, a nonwoven fabric such as an air-through nonwoven fabric which is a sheet material having a good texture may be disposed between the first sheet 122A of the steam generator 120 and the wearer (not shown). In this case, it is preferable that the nonwoven fabric has the air permeability so as not to inhibit the passage of the steam. Furthermore, it is more preferable that the nonwoven fabric has water repellency so as not to inhibit the passage of the steam and not to inhibit the inflow of air due to wetting of the nonwoven fabric with the steam.

Such a nonwoven fabric may be formed on the first sheet 122A of the steam generator 120, and may be a nonwoven fabric which is attached to the surface of the mask 110 on the side of the wearer so as to be freely opened and closed, and which is closed after attaching the steam generator 120.

[Adhesive]

In the present embodiment, the adhesive 106 is provided on the surface opposite to the side of the wearer of the steam generator 120, that is, on the surface opposite to the side of the wearer of the second sheet 122B. As a result, it possible to stably fix the steam generator 120 to the mask 110.

The adhesive 106 may fix at least the steam generator 120 to the mask body portion 101, and the size and the shape are not particularly limited.

As the adhesive 106, a hot melt adhesive is preferably used. The hot melt adhesive normally contains an adhesive base, a tackifier resin, and a softening agent as constituents. Examples of the type of the hot melt adhesive include synthetic rubber type, polyolefin type (Polyethylene (PE) type, Ethylene Vinyl Acetate (EVA) type, Ethylene-Ethyl-Acrylate (EEA) type, Atactic Polypropylene (APP) type, Amorphous PolyAlpha Olefin (APAO) type), polyamide type (nylon type and polyamide type), polyester type, acrylic type, and the like. These may be used alone or in combination of two or more types. In particular, from the viewpoints of preservability, adhesive strength, and safety, synthetic rubber type, polyolefin type, acrylic type, and polyamide type are preferable, and synthetic rubber type is particularly preferable.

The adhesive 106 is protected and not adhered to the outside by a release paper in a state before use of the steam heating mask 100. The release paper is not particularly limited and can be used.

The adhesive may be provided on the surface of the mask body portion 101 on the side of the wearer. Specifically, the adhesives are symmetrically provided in pairs in the vicinity of the folding line 103 of the mask body portion 101, and in the vicinity of the upper end of the mask body portion 101. As a result, the fixing position of the steam generator 120 can be easily understood. In this case, it is preferable to use an adhesive that can be used repeatedly.

Although the embodiments of the present invention are described with reference to the drawings, these are examples of the present invention, and various configurations other than those described above can be adopted.

For example, although in each of the above embodiments, the example in which two steam generators 120 are separately attached to the mask 110 is described, a structure in which the two steam generators 120 are connected by one bag body may be adopted.

In addition, although in each of the above embodiments, the example in which the mask body portion 101 is formed by one sheet and folded symmetrically with the folding line 103 is described, the mask body portion 101 may be one in which two sheets of the same shape are superimposed and the folding lines 103 are formed by bonding one side. The sheet used in this case can use the same sheets as those described in each of the above embodiments.

Regarding the above embodiments, the present invention further discloses the following composition, manufacturing method, or application.

<1> A steam heating mask that includes a mask which includes a mask body portion covering a nose and a mouth of a wearer when wearing the mask, and a pair of ear hook portions provided at both left and right ends of the mask body portion, and a steam generator on the mask body portion, in which a proportion of an area occupied by the steam generator is equal to or greater than 30% and equal to or less than 80% with respect to an area of an entire surface of the mask body portion on a side of the wearer, the steam generator accommodates inside a steam generating portion, the steam generator includes a first sheet on a surface of the steam generating portion on the side of the wearer, and a second sheet on a surface opposite to the surface on the side of the wearer, of the steam generating portion, a degree of air permeability of the first sheet is equal to or less than 7,000 sec/100 ml, and a degree of air permeability of the second sheet is greater than 8,000 seconds/100 ml.

<2> A steam heating mask that includes a mask which includes a mask body portion covering a nose and a mouth of a wearer when wearing the mask, and a pair of ear hook portions provided at both left and right ends of the mask body portion, and a steam generator on the mask body portion, in which a proportion of an area occupied by the steam generator is equal to or greater than 30% and equal to or less than 80% with respect to an area of an entire surface of the mask body portion on a side of the wearer, the steam generator accommodates inside a steam generating portion, the steam generator includes a first sheet on a surface of the steam generating portion on the side of the wearer, and a second sheet on a surface opposite to the surface on the side of the wearer, of the steam generating portion, a degree of air permeability of the second sheet is equal to or greater than 250 sec/100 ml and equal to or less than 8,000 sec/100 ml, and a degree of air permeability of the first sheet is equal to or less than 20% with respect to the degree of air permeability of the second sheet.

<3> The steam heating mask according to <1> or <2>, in which the stiffness value in the vertical direction of the steam generator is preferably equal to or greater than 30 gf/60 mm width, more preferably equal to or greater than 60 gf/60 mm width, and still more preferably equal to or greater than 70 gf/60 mm width.

<4> The steam heating mask according to any one of <1> to <3>, in which the stiffness value in the vertical direction of the steam generator is preferably equal to or less than 150 gf/60 mm width, more preferably equal to or less than 130 gf/60 mm width, and still more preferably equal to or less than 120 gf/60 mm width.

<5> The steam heating mask according to any one of <1> to <4>, in which the maximum absolute humidity in the mask during use of the steam heating mask in the present embodiment is preferably equal to or greater than 12 $g/m^3$, more preferably equal to or greater than 13 $g/m^3$, still more preferably equal to or greater than 15 $g/m^3$, still more preferably equal to or greater than 20 $g/m^3$, and even more preferably equal to or greater than 25 $g/m^3$.

<6> The steam heating mask according to any one of <1> to <5>, in which the maximum absolute humidity in the mask during use of the steam heating mask is preferably equal to or less than 50 $g/m^3$, more preferably equal to or less than 45 $g/m^3$, still more preferably equal to or less than 40 $g/m^3$, and even more preferably equal to or less than 35 $g/m^3$.

<7> The steam heating mask according to any one of <1> to <6>, in which an air permeation resistance of the mask body portion is preferably equal to or greater than 5 Pa, more preferably equal to or greater than 20 Pa, and still more preferably equal to or greater than 50 Pa.

<8> The steam heating mask according to any one of <1> to <7>, in which an air permeation resistance of the mask body portion is preferably equal to or less than 200 Pa, more preferably equal to or less than 190 Pa, and still more preferably equal to or less than 180 Pa.

<9> The steam heating mask according to any one of <1> to <8>, in which the basis weight of the mask body portion is preferably equal to or greater than 5 $g/m^2$, more preferably equal to or greater than 10 $g/m^2$, and still more preferably equal to or greater than 30 $g/m^2$.

<10> The steam heating mask according to any one of <1> to <9>, in which the basis weight of the mask body portion is preferably equal to or less than 200 $g/m^2$, more preferably equal to or less than 150 $g/m^2$, and still more preferably equal to or less than 120 $g/m^2$.

<11> The steam heating mask according to any one of <1> to <10>, in which the steam generating portion includes an oxidizable metal, a water absorbing agent, water, and an electrolyte.

<12> The steam heating mask according to <11>, in which the content of the water absorbing agent is preferably equal to or greater than 0.3 parts by mass, more preferably equal to or greater than 1 part by mass, and still more preferably equal to or greater than 3 parts by mass, with respect to 100 parts by mass of the oxidizable metal.

<13> The steam heating mask according to <11> or <12>, in which the content of the water absorbing agent is preferably equal to or less than 100 parts by mass, more preferably equal to or less than 80 parts by mass, and still more preferably equal to or less than 60 parts by mass, with respect to 100 parts by mass of the oxidizable metal.

<14> The steam heating mask according to any one of <11> to <13>, in which the moisture content of the steam generating portion is preferably equal to or greater than 35 parts by mass, more preferably equal to or greater than 40 parts by mass, and still more preferably equal to or greater than 50 parts by mass with respect to 100 parts by mass of the oxidizable metal.

<15> The steam heating mask according to any one of <11> to <14>, in which the moisture content of the steam generating portion is preferably equal to or less than 200 parts by mass, more preferably equal to or less than 150 parts by mass, still more preferably equal to or less than 100 parts by mass, and even more preferably equal to or less than 80 parts by mass with respect to 100 parts by mass of the oxidizable metal.

<16> The steam heating mask according to any one of <1> to <15>, in which the steam generation amount of the steam generator is preferably equal to or greater than 30 mg/cell·10 min, more preferably equal to or greater than 50 mg/cell·10 min, still more preferably equal to or greater than 150 mg/cell·10 min, still more preferably equal to or greater than 250 mg/cell·10 min, and even more preferably equal to or greater than 300 mg/cell·10 min, as a whole of the steam generator.

<17> The steam heating mask according to any one of <1> to <16>, in which the steam generation amount of the steam generator is preferably equal to or less than 1,200 mg/cell·10 min, more preferably equal to or less than 1,000 mg/cell·10 min, still more preferably equal to or less than 800 mg/cell·10 min, still more preferably equal to or less than 700 mg/cell·10 min, and even more preferably equal to or less than 500 mg/cell·10 min, as a whole of the steam generator.

<18> The steam heating mask according to any one of <1> to <17>, in which the steam generation amount per unit area of the steam generator is preferably equal to or greater than 1 mg/cm$^2$·10 min, more preferably equal to or greater than 1.5 mg/cm$^2$·10 min, still more preferably equal to or greater than 5 mg/cm$^2$·10 min, still more preferably equal to or greater than 7 mg/cm$^2$·10 min, and even more preferably equal to or greater than 9 mg/cm$^2$·10 min, as a whole of the steam generator.

<19> The steam heating mask according to any one of <1> to <18>, in which the steam generation amount per unit area of the steam generator is preferably equal to or less than 20 mg/cm$^2$·10 min, more preferably equal to or less than 18 mg/cm$^2$·10 min, and still more preferably equal to or less than 15 mg/cm$^2$·10 min, as a whole of the steam generator.

<20> The steam heating mask according to any one of <1> to <19>, in which the steam generation amount of the steam heating mask is preferably equal to or greater than 60 mg/10 min, more preferably equal to or greater than 100 mg/10 min, still more preferably equal to or greater than 300 mg/10 min, still more preferably equal to or greater than 500 mg/10 min, and even more preferably equal to or greater than 600 mg/10 min.

<21> The steam heating mask according to any one of <1> to <20>, in which the steam generation amount of the steam heating mask is preferably equal to or less than 2,000 mg/10 min, more preferably equal to or less than 1,400 mg/10 min, and still more preferably equal to or less than 1,000 mg/10 min.

<22> The steam heating mask according to any one of <1> to <21>, in which the average absolute humidity in the mask during use of the steam heating mask is preferably equal to or greater than 11.7 g/m$^3$, more preferably equal to or greater than 12 g/m$^3$, still more preferably equal to or greater than 13 g/m$^3$, still more preferably equal to or greater than 15 g/m$^3$, and even more preferably equal to or greater than 19 g/m$^3$.

<23> The steam heating mask according to any one of <1> to <22>, in which the average absolute humidity in the mask during use of the steam heating mask is preferably equal to or less than 35 g/m$^3$, more preferably equal to or less than 30 g/m$^3$, and still more preferably equal to or less than 25 g/m$^3$.

EXAMPLE

Embodiments of the present invention will be described more specifically by the following examples. The examples are for description and do not limit the scope of the present invention.

Example A

Example A1

A steam heating mask 100 similar to the mask described in the first embodiment was prepared. Specifically, it is as follows.

<Preparation of Steam Generating Portion 121>

A heat generation composition having the composition shown in Table 1 was prepared by the following procedure.

The thickener was dissolved in water, and thereafter an aqueous solution was prepared by dissolving tripotassium phosphate. On the other hand, a powder premixed with iron powder and activated carbon was prepared, and the premixed powder was placed in the aqueous solution and stirred with a disk turbine type stirring blade at 150 rpm for 10 minutes to obtain a slurry-like heat generation composition.

The obtained heat generation composition was coated to one side of the base material layer 121B using a die coating method so as to be 1.4 g per one (4.9 cm×4.9 cm; area 24.0 cm$^2$) of the steam generating portion 121. Salt (Normal Sodium Chloride (manufactured by Otsuka Pharmaceutical Co., Ltd.)) was sprayed on the coated surface so as to be 0.07 g per one (same as above) of the steam generating portion 121 to form the steam generating layer 121A, and the water retaining sheet 121C was superposed thereon to prepare the steam generating portion 121.

As the base material layer 121B, a polyethylene film having a basis weight of 27 g/m$^2$ was used. As the water retaining sheet 121C, a polymer sheet integrally formed by laminating wood pulp paper (basis weight 20 g/m$^2$, manufactured by Ino Paper Co., Ltd.), water absorbent polymer (sodium polyacrylate, spherical, average particle diameter 300 μm, basis weight 50 g/m$^2$, Aqualic CA, manufactured by Nippon Shokubai Co., Ltd.), and wood pulp paper (basis weight 30 g/m$^2$, manufactured by Ino Paper Co., Ltd.) was used.

The steam generating portion 121 obtained in this manner was superposed in two layers (mass 3.43 g) so that the water retaining sheet 121C was disposed on the skin side (first sheet 122A side). The moisture content in the steam generating portion 121 immediately after preparation was 62 parts by mass with respect to 100 parts by mass of the iron powder.

TABLE 1

| | Components | Parts by mass |
|---|---|---|
| Iron powder | Iron powder RKH: manufactured by DOWA Electronics Materials Co., Ltd. | 100 |
| Activated carbon | Carboraffin: manufactured by Japan EnviroChemicals Co., Ltd. | 8 |
| Thickener | Xanthan gum: DSP Gokyo Food & Chemical Co., Ltd. | 0.25 |
| pH adjuster | Tripotassium phosphate: Yoneyama Chemical Industry Co., Ltd. | 1.8 |
| Water | Deionized water | 62 |
| | Total | 172.05 |

<Preparation of Steam Generator 120>

The obtained entire steam generating portion 121 was covered with the bag body 122 including the first sheet 122A and the second sheet 122B having the degree of air permeability as shown in Table 3 to prepare the steam generator 120. Specifically, as the first sheet 122A (hereinafter the same) of the steam generator 120, two sheets of TMS nonwoven fabric (thermal bond (PET/PE)-meltblown (polypropylene)-spunbond (polypropylene) laminated integrated type, basis weight 50 g/m$^2$, manufactured by Kuraray Co., Ltd.) were laminated to obtain a sheet having the degree of air permeability of 0 sec/100 ml. As the second sheet 122B (hereinafter the same) of the steam generator 120, a non-air permeable sheet having a basis weight of 40 g/m$^2$ laminated with a 100% by mass polyethylene film and a pulp sheet was used.

The steam generating portion 121 was disposed between the first sheet 122A and the second sheet 122B to hermetically seal the peripheral edge portion to obtain the steam generator 120. At this time, the base material layer 121B of the steam generating portion 121 was disposed on the side of the second sheet 122B. At this time, the area of the first sheet 122A including the air permeation surface and the seal portion was 39.7 cm$^2$ (6.3 cm×6.3 cm).

The steam generator 120 was stored in the oxygen blocking bag until evaluation to be described later was performed.

<Preparation of Steam Heating Mask 100>

As a sheet of the mask body portion 101 constituting the mask 110, two layers were laminated so that the SMS nonwoven fabric (spunbond (polypropylene)-meltblown (polypropylene)-spunbond (polypropylene) laminated integrated type, basis weight 50 g/m$^2$) was on the outside and the spunbonded nonwoven fabric (polypropylene) with a basis weight of 25 g was on the inside (on the side of the wearer). At this time, a blocking ratio of particles of equal to or greater than 0.3 μm in the mask body portion 101 was 25%. Each one on the upper side of both sides across the folding line 103 at the longitudinal center of the mask body portion 101 (two in total), other than the upper portion of the mask of the accommodation body 104, was thermally fused to prepare an accommodation body 104 accommodating the steam generator 120. The ear hook portion 102 having an elastic rubber string shape was attached to the end portion of the mask body portion 101, and a mask 110 having a three-dimensional shape was prepared. The air permeation resistance of the mask body portion 101 was measured at the accommodation body portion to be 148 Pa/30 mm Φ·pressure difference. In the following evaluation, each one of the steam generators 120 (two in total) is placed in the accommodation body 104 from the upper side of the mask 110 to which two nonwoven fabrics of the mask body portion 101 are not thermally fused, and a pair of steam generators 120 were attached symmetrically in the vicinity of the folding line 103 of the mask body portion 101 and in the vicinity of the upper end portion (nasal side) of the mask body portion 101 to form a steam heating mask 100.

In the present example, the area of the entire surface of the mask body portion 101 on the side of the wearer was calculated by the following method.

The mask body portion 101 was folded in the longitudinal direction at the center portion, the end portion on the ear-hook side of the seal portion was set as a tip end of the mask at a point on the folding line which is farthest from a line (A line) connecting upper and lower points that are farthest apart from each other vertically in the direction of the tip end, was cut off by a line (C line) spaced in parallel by 7 cm in the direction of the ear hook from a line (B line) parallel to the A line passing through the tip end of the mask, and the seal portion was further cut off. The outer periphery of one side of the cut mask body was traced on A4 paper (recycle cut type G80A4W, manufactured by Toppan Forms Co., Ltd., basis weight 64 g/m$^2$, 21.0 cm×29.7 cm: area 623.7 cm$^2$), the outer periphery thereof was cut with scissors, and the mass of the cut paper was measured. When converted from the total mass of the A4 paper, twice the mass of the cut paper, and the total area of A4 paper, the area of the entire surface of the mask body portion 101 on the side of the wearer is 152.0 cm$^2$, and the area ratio of the two left and right steam generators 120 with respect to the area of the entire surface of the mask body portion 101 on the side of the wearer was 52%.

(Examples A2 and A3)

As the first sheet 122A of the steam generator 120, a synthetic pulp paper having the degree of air permeability of 4.0 sec/100 ml and a basis weight of 40 g/m$^2$ (trade name: Eleven MOA, manufactured by Tokai Pulp Co., Ltd.) was used, and one sheet of synthetic pulp paper was stacked in Example A2, and two sheets were stacked in Example A3. A steam heating mask 100 was prepared in the same manner as in Example A1, except that.

Examples A4 to A8

A steam heating mask 100 was prepared in the same manner as in Example A1, except that a calcium carbonate-containing polyethylene film having the degree of air permeability shown in Table 3 and a basis weight of 50 g/m$^2$ (trade name: TSF-EU, manufactured by Kohjin Co., Ltd.) was used as the first sheet 122A of the steam generator 120.

Examples A9 to A11

A steam heating mask 100 was prepared in the same manner as in Example A1, except that a calcium carbonate-containing polyethylene film having the degree of air permeability shown in Table 3 and a basis weight of 50 g/m$^2$ (trade name: TSF-EU, manufactured by Kohjin Co., Ltd.) was used as the second sheet 122B of the steam generator 120.

Examples A12, A13 and Comparative Example A1

The steam generating portion 121 (4.9 cm×4.9 cm; area 24.0 cm$^2$) of Example A1 was cut into a size of 3.3 cm×3.3 cm (area 10.9 cm$^2$) and) used as a steam generating portion.

In addition, in the preparation of the steam generator, the sizes of the first sheet and the second sheet were set to 4.8 cm×4.8 cm (area 23.0 cm$^2$) in Example A12, 5.5 cm×5.5 cm (area 30.3 cm$^2$) in Example A13, and 3.9 cm×3.9 cm (area 15.2 cm$^2$) in Comparative Example A1, the steam generating portions 121 were disposed between the respective sheets, and the peripheral edge portions were hermetically sealed to obtain the steam generators 120. The steam heating mask 100 was prepared in the same manner as in Example A1 except that, so that the area ratio of the steam generator 120 with respect to the area of the entire surface of the mask body portion 101 on the side of the wearer was set as shown in Table 3.

Examples A14, A15 and Comparative Example A2

In the preparation of the steam generating portion 121, when die-coating the heat generation composition on one side of the base material layer 121B, the size of one of the steam generating portions 121 was set to 4.9 cm×6.5 cm (area 31.9 cm$^2$) in Example A14, 4.9 cm×7.5 cm (area 36.8 cm$^2$) in Example A15, and 4.9 cm×8.5 cm (area 41.7 cm$^2$) in Comparative Example A2, and the heat generation composition was prepared so that the coating amount of the heat generation composition has the same thickness (1.4 g when converted per 4.9 cm×4.9 cm) as that in Example A1. In addition, in the preparation of the steam generator, the sizes of the first sheet and the second sheet were set to 6.3 cm×8.4 cm (area 52.9 cm$^2$) in Example A14, 6.3 cm×9.6 cm (area 60.5 cm$^2$) in Example A15, and 6.4 cm×10.6 cm (area 67.8 cm$^2$) in Comparative Example A2, the steam generating portions 121 were disposed between the respective sheets, and the peripheral edge portions were hermetically sealed to obtain the steam generators 120. The steam heating mask 100 was prepared in the same manner as in Example A1 except that, so that the area ratio of the steam generator 120 with respect to the area of the entire surface of mask body portion 101 on the side of the wearer was set as shown in Table 3.

Examples A16 and A17

A steam generator 120 was prepared according to Example A1, except that only one layer of the steam generating portion 121 used in Example A1 was used as the steam generating portion, and the first sheet having a degree of air permeability shown in Table 3 was used. In the Example A16, a steam heating mask 100 was prepared in the same manner as in Example A1 except that. In the Example A17, a steam heating mask 100 was prepared by laminating one sheet of ADVANTEC (registered trademark) qualitative filter paper No. 2 cut to a size of 63 mm square so as to be in contact with the second sheet of the steam generator in addition to the prepared steam generator at the time of preparing a steam heating mask.

Examples A18 and A19

A powdery heat generation composition having the composition shown in Table 2 was prepared as a steam generating portion by the following procedure.

In a nitrogen stream, iron powder, water, salt, water absorbing polymer, and activated carbon were mixed until uniform, and a powdery steam generating portion was prepared. In the preparation of the steam generator 120, the steam heating mask 100 was prepared in the same manner as in Example A1, except that 2.8 g of the powdery steam generating portion was respectively used instead of the sheet-like steam generating portions 121 in Example A1 for Example A18, and in Example A8 for Example A19.

TABLE 2

| Components | | Parts by mass |
|---|---|---|
| Iron powder | Iron powder RKH: manufactured by DOWA Electronics Materials Co., Ltd. | 100 |
| Activated carbon | Carboraffin: manufactured by Japan EnviroChemicals Co., Ltd. | 34.1 |
| Water absorbing polymer | Aquapearl A3: manufactured by San-Dia Polymers Co., Ltd. | 23.7 |
| Salt | — | 5.05 |
| Water | Deionized water | 152.7 |
| | Total | 315.55 |

Comparative Examples A3 and A4

A steam heating mask 100 was prepared in the same manner as in Example A1, except that a calcium carbonate-containing polyethylene film having a basis weight of 50 g/m$^2$, TSF-EU, manufactured by Koshin Co., Ltd. was used and a film having the degree of air permeability of 8,000 sec/100 ml was used for Comparative Example A3, and the degree of air permeability of 10,000 sec/100 ml was used for Comparative Example A4 as the first sheet 122A of the steam generator 120.

The oxygen blocking bag (packaging material) was opened, the prepared steam generator 120 was taken out, quickly set on the mask 110, and the following evaluation was performed. The results are shown in Table 3.

[Measurement of Stiffness Value of Steam Generator]

Using a Tensilon universal testing machine (ORIENTEC RTC-1150A), the bending stiffness value of the mask set was measured. The bending stiffness value was measured in a state where one folding line of the mask body was cut out and one cell of the steam generator was inserted in the mask accommodation body using one side of the mask. Measurement conditions were as follows: a steam generator was supported at a span distance of 30 mm, and a plate-shaped pressing member having a width of 60 mm and a tip radius of 5 mm was used to apply a load at a cross head speed of 20 mm/min to the center of a test piece (steam generator). The peak load at this time (average value of 3 measurements) was taken as the stiffness value.

[Measurement of Steam Generation Amount (Steam Generator)]

A test machine capable of supplying dry air of 2.1 liters/min in a closed system having an internal volume of 4.2 liters and an internal humidity of 1 RH % was prepared, and a steam generator 120 having a predetermined size is allowed to stand to generate heat so that the steam can be evaporated inside the test machine. The humidity of the air discharged to the outside of the closed system was measured with a hygrometer and the amount of steam generated after the start of heat generation was determined using the following formula (1) to obtain the amount of steam per unit time. e is steam pressure (Pa), es is saturated steam pressure (Pa: quoted from JIS Z8806), T is temperature (° C.: dry bulb temperature), and s is sampling period (sec).

$$\text{Relative humidity } U \ (\% \ RH) = (e/es) \times 100 \quad (1)$$

$$\text{Absolute humidity } D \ (g/m^3) =$$
$$(0.794 \times 10^{-2} \times e)/(1 + 0.00366T) =$$
$$(0.794 \times 10^{-2} \times U \times es)/[100 \times (1 + 0.00366T)]$$

$$\text{Unit air volume } P \ (\text{liter}) = (2.1 \times s)/60$$

$$\text{Amount of steam generation per unit time } A \ (g) = (P \times D)/1{,}000$$

[Swelling of Steam Heating Element]

30 minutes after wearing the mask to the head model mannequin prepaid using male human head data (average of 52 Japanese adult men) of Digital Human Technology Co., Ltd. (hereinafter referred to as "mannequin") under the environment of 20° C. and 60% RH, the steam generator was taken out from the mask body, the gas inside the steam generator (inside closed by skin side sheet and outside sheet) was aspirated with a syringe, and the volume was measured. Two measurements were performed and the average was used as the measured value.

[Measurement of Steam Generation Amount (Steam Heating Mask)]

The steam generation amount was measured by the above-described method for measuring the amount of steam generation performed on the steam generator.

[Measurement of Air Permeation Resistance of Mask Body Portion 101]

The air permeation resistance of the mask body portion 101 was measured using a mask tester MTS-2 (Shibata Science). On the upper portion of the body of the mask tester MTS-2 (Shibata Science), a sheet cut out into a size of 3.5 cm×3.5 to 5 cm×5 cm was disposed from the sheet material of the mask body portion 101 and fixed with a sheet fixing jig so as not to leak. The measurement was performed at the test area of 7 cm² (3 cm φ) and the test flow rate of 10 L/min for 10 seconds. The air permeation resistance was 148 Pa when the value was determined from the differential pressure between the air inflow side (inlet side) and the air outflow side (outlet side) to the sheet.

[Measurement of Absolute Humidity in Mask]

At an environment of 20° C. and 60% RH, the temperature and humidity sensor (SHT 75 manufactured by Sensirion Co., Ltd.) is attached to the lower portion of the nose of the mannequin, and air is inhaled at a frequency of 500 ml each time and 15 times per minute from the nose portion of the head model, using a ventilator ((HARVARD APPARATUS DUAL PHASE CONTROL RESPIRATOR (manufactured by HARVARD APPARATUS Co., Ltd.)) and simulating a human respiratory rhythm. In this state, the steam heating mask 100 was attached to the mannequin, the change in temperature and humidity was measured. The absolute humidity was calculated from the temperature and relative humidity, and the maximum absolute humidity and the average absolute humidity for 10 minutes were obtained.

[Evaluation of Feeling of Wearing of Mask (Warm Feeling, Durability, Steam Feeling (Moist Feeling), and Feeling of Stuffiness)]

At the environment of 22° C., the feeling of wearing the mask was evaluated by a panel of five men. The warming feeling, durability, steam feeling (moist feeling), and feeling of stuffiness in the state of wearing the mask were evaluated according to the following criteria, and the score with the largest number of people was selected and scored.

Warming Feeling

1: Hard to feel the difference in warmth, as compared with the mask body only

2: Warm, as compared with the mask body only

3: Sufficiently warm and adequate warming feeling, as compared with the mask body only 4: Sufficiently warm and slightly hot, as compared with the mask body only 5: Sufficiently warm and hot, as compared with the mask body only Durability 1: Less than 5 minutes duration of comfortable warming feeling and steam feeling 2: Equal to or greater than 5 and less than 10 minutes duration of comfortable warming feeling and steam feeling 3: Equal to or greater than 10 minutes duration of comfortable warming feeling and steam feeling Steam Feeling (Moist Feeling)

1: Hard to feel the difference in moisture in the mucosa of throat and nose, as compared with the mask body only 2: Slightly feel the moisture in the mucosa of throat and nose, as compared with the mask body only 3: Feel the moisture in the mucosa of throat and nose, as compared with the mask body only 4: Excellent in moist feeling in the mucosa of throat and nose, as compared with the mask body only 5: Very excellent in moist feeling in the mucosa of throat and nose, as compared with the mask body only Feeling of Stuffiness 1: Very stuffy, as compared with the mask body 2: Quite stuffy, as compared with the mask body 3: Slightly feel stuffy, as compared with the mask body 4: Feel little stuffy, as compared with the mask body 5: Does not feel any stuffy, equivalent to the mask body

TABLE 3

| | Physical properties | Example | | | | | | | | | | | |
|---|---|---|---|---|---|---|---|---|---|---|---|---|---|
| | | A1 | A2 | A3 | A4 | A5 | A6 | A7 | A8 | A9 | A10 | A11 | A12 |
| Steam generator | Degree of air permeability (sec/100 ml) of first sheet 122A (skin side sheet) | 0 | 4.0 | 8.1 | 250 | 630 | 2500 | 5000 | 7000 | 0 | 0 | 0 | 0 |
| | Degree of air permeability (sec/100 ml) of second sheet 122B (outside sheet) | Non-air permeable | Non-air permeable | Non-air permeable | Non-air permeable | Non-air permeable | Non-air permeable | Non-air permeable | Non-air permeable | 8200 | 10000 | 30000 | Non-air permeable |

TABLE 3-continued

| | | | | | | | | | | | | | |
|---|---|---|---|---|---|---|---|---|---|---|---|---|---|
| | Type of steam generation portion | Coated type (2 sheets) | ← | ← | ← | ← | ← | ← | ← | ← | ← | ← | ← |
| | Area of steam generation portion (cm²) | 24.0 | ← | ← | ← | ← | ← | ← | ← | ← | ← | ← | 10.9 |
| | Area of steam generator (cm²) | 39.7 | 39.7 | 39.7 | 39.7 | 39.7 | 39.7 | 39.7 | 39.7 | 39.7 | 39.7 | 39.7 | 23.0 |
| | Stiffness value (gf/60 mm width in a vertical direction) | 108.0 | 85.0 | 111.0 | 62.3 | 60.0 | 68.3 | 79.7 | 84.7 | 76.3 | 59.0 | 62.0 | 72.0 |
| | Steam generation amount (mg/cell · 10 min) | 365 | 341 | 322 | 352 | 260 | 166 | 57 | 38 | 360 | 401 | 376 | 148 |
| | Steam generation amount (mg/cm² · 10 min) | 9.2 | 9.2 | 8.1 | 8.9 | 6.6 | 4.2 | 1.4 | 1.0 | 9.1 | 10.1 | 9.5 | 6.4 |
| Steam heating mask | Area ratio of steam generator | 52% | 52% | 52% | 52% | 52% | 52% | 52% | 52% | 52% | 52% | 52% | 30% |
| | Swelling of steam heating mask (ml, one cell · 30 minutes later) | 0.0 | 0.0 | 0.0 | 9.5 | 12.0 | 0.0 | 0.0 | 0.0 | 0.0 | 0.0 | 0.0 | 0.0 |
| | Steam generation amount of steam heating mask (mg/10 min) | 730 | 681 | 645 | 705 | 520 | 332 | 114 | 76 | 720 | 802 | 753 | 297 |
| | Maximum absolute humidity (g/m3)/using mannequin | 31.3 | 25.7 | 29.9 | 28.9 | 23.9 | 20.0 | 13.9 | 13.4 | 30.4 | 27.8 | 28.4 | 17.1 |
| | Average absolute humidity (g/m3) for 10 minutes/using mannequin | 23.3 | 19.1 | 20.8 | 21.1 | 18.9 | 15.4 | 12.5 | 12.3 | 21.3 | 20.0 | 20.3 | 14.4 |
| Evaluation | Warm feeling | 3 | 3 | 3 | 4 | 3 | 3 | 3 | 2 | 3 | 3 | 3 | 3 |
| | Durability | 2 | 2 | 2 | 3 | 3 | 3 | 3 | 1 | 2 | 2 | 2 | 1 |
| | Steam feeling (moist feeling) | 5 | 4 | 4 | 5 | 4 | 3 | 2 | 2 | 5 | 5 | 5 | 3 |
| | Feeling of Stuffiness | 5 | 5 | 5 | 4 | 4 | 5 | 5 | 5 | 5 | 5 | 5 | 5 |

| | Physical properties | Example | | | | | | | Comparative Example | | | |
|---|---|---|---|---|---|---|---|---|---|---|---|---|
| | | A13 | A14 | A15 | A16 | A17 | A18 | A19 | A1 | A2 | A3 | A4 |
| Steam generator | Degree of air permeability (sec/100 ml) of first sheet 122A (skin side sheet) | 0 | 0 | 0 | 2500 | 2500 | 0 | 7000 | 0 | 0 | 8000 | 10000 |
| | Degree of air permeability (sec/100 ml) of second sheet 122B (outside sheet) | Non-air permeable | Non-air permeable | Non-air permeable | Non-air permeable | Non-air permeable | Non-air permeable | Non-air permeable | Non-air permeable | Non-air permeable | Non-air permeable | Non-air permeable |
| | Type of steam generation portion | ← | ← | ← | ← (1 sheet) | ← + Stiff body | Powder | Powder | Coated type (2 sheets) | ← | ← | ← |
| | Area of steam generation portion (cm²) | 10.9 | 31.9 | 36.8 | 24.0 | ← | — | — | 10.9 | 41.7 | 24.0 | 24.0 |
| | Area of steam generator (cm²) | 30.3 | 52.9 | 60.5 | 39.7 | 39.7 | 39.7 | 39.7 | 15.2 | 67.8 | 39.7 | 39.7 |

TABLE 3-continued

|   |   |   |   |   |   |   |   |   |   |   |   |   |
|---|---|---|---|---|---|---|---|---|---|---|---|---|
|   | Stiffness value (gf/60 mm width in a vertical direction) | 75.7 | 108.3 | 113.3 | 35.0 | 134.7 | 70.0 | 50.3 | 78.3 | 115.3 | 86.7 | 93.3 |
|   | Steam generation amount (mg/cell · 10 min) | 158 | 440 | 586 | 71 | 71 | 360 | 42 | 157 | 598 | 18 | 22 |
|   | Steam generation amount (mg/cm² · 10 min) | 5.2 | 8.3 | 9.7 | 1.8 | 1.8 | 9.1 | 1.1 | 10.3 | 8.8 | 0.5 | 0.6 |
| Steam heating mask | Area ratio of steam generator | 40% | 70% | 80% | 52% | 52% | 52% | 52% | 20% | 90% | 52% | 52% |
|   | Swelling of steam heating mask (ml, one cell · 30 minutes later) | 0.0 | 0.0 | 0.0 | 0.0 | 0.0 | 0.0 | 0.0 | 0.0 | 0.0 | 0.0 | 0.0 |
|   | Steam generation amount of steam heating mask (mg/10 min) | 317 | 879 | 1171 | 142 | 142 | 721 | 85 | 314 | 1197 | 36 | 44 |
|   | Maximum absolute humidity (g/m3)/using mannequin | 17.7 | 34.0 | 34.7 | 14.0 | 14.7 | 24.1 | 12.2 | 14.3 | 28.6 | 11.9 | 11.7 |
|   | Average absolute humidity (g/m3) for 10 minutes/using mannequin | 15.0 | 23.8 | 24.6 | 12.7 | 13.3 | 20.6 | 11.9 | 12.9 | 21.9 | 11.5 | 11.2 |
| Evaluation | Warm feeling | 3 | 4 | 4 | 3 | 3 | 3 | 3 | 1 | 5 | 2 | 1 |
|   | Durability | 2 | 2 | 2 | 2 | 2 | 2 | 2 | 1 | 2 | 1 | 1 |
|   | Steam feeling (moist feeling) | 3 | 5 | 5 | 3 | 3 | 5 | 2 | 2 | 5 | 1 | 1 |
|   | Feeling of Stuffiness | 5 | 5 | 4 | 4 | 5 | 5 | 5 | 5 | 2 | 5 | 5 |

Example B

Example B1

A steam heating mask 100 having the same shape as in above Example A was prepared. Specifically, it is as follows.
<Preparation of Steam Generating Portion 121>
Using the heat generation composition having the composition shown in Table 1, the steam generating portion 121 was prepared in the same manner as in Example A1.
<Preparation of Steam Generator 120>
The obtained entire steam generating portion 121 was covered with the bag body 122 including the first sheet 122A and the second sheet 122B having the degree of air permeability as shown in Table 4 to prepare the steam generator 120. Specifically, as the first sheet 122A (hereinafter the same) of the steam generator 120, two sheets of TMS nonwoven fabric (thermal bond (PET/PE)-meltblown (polypropylene)-spunbond (polypropylene) laminated integrated type, basis weight 50 g/m², manufactured by Kuraray Co., Ltd.) were laminated to obtain a sheet having the degree of air permeability of 0 sec/100 ml. As the second sheet 122B (hereinafter the same) of the steam generator 120, a polyethylene film containing calcium carbonate having the degree of air permeability of 7,000 sec/100 ml and a basis weight of 50 g/m² (trade name: TSF-EU, manufactured by Kohjin Co., Ltd.) was used. The steam generating portion 121 was disposed between the first sheet 122A and the second sheet 122B to hermetically seal the peripheral edge portion to obtain the steam generator 120. At this time, the base material layer 121B of the steam generating portion 121 was disposed on the side of the second sheet 122B. At this time, the area of the air permeation surface (first sheet 122A) was set to be 6.3 cm×6.3 cm (area 39.7 cm²) (area ratio of the steam generating portion 121 with respect to the area of the air permeation surface is 60.5%).

The steam generator 120 was stored in the oxygen blocking bag until evaluation to be described later was performed.
<Preparation of Steam Heating Mask 100>
The steam heating mask 100 was prepared in the same manner as in Example A1.

Examples B2 and B3

As the first sheet 122A of the steam generator 120, a synthetic pulp paper having the degree of air permeability of 4.0 sec/100 ml and a basis weight of 40 g/m² (trade name: Eleven MOA, manufactured by Tokai Pulp Co., Ltd.) was used, and one sheet of synthetic pulp paper was stacked in Example B2, and two sheets were stacked in Example B3. A steam heating mask 100 was prepared in the same manner as in Example B1, except that.

Example B4

As the first sheet 122A of the steam generator 120, a calcium carbonate-containing polyethylene film having the degree of air permeability of 250 sec/100 ml and a basis weight of 50 g/m² (trade name: TSF-EU, manufactured by Kohjin Co., Ltd.) was used. A steam heating mask 100 was prepared in the same manner as in Example B1, except that.

Examples B5 to B9

A steam heating mask 100 was prepared in the same manner as in Example B1, except that a calcium carbonate-containing polyethylene film having the degree of air permeability shown in Table 4 and a basis weight of 50 g/m² (trade name: TSF-EU, manufactured by Kohjin Co., Ltd.) was used as the second sheet 122B of the steam generator 120.

Examples B10, B11 and Comparative Example B1

The steam generating portion 121 (4.9 cm×4.9 cm; area 24.0 cm²) of Example B1 was cut into a size of 3.3 cm×3.3 cm (area 10.9 cm²) and used as a steam generating portion. In addition, in the preparation of the steam generator, the sizes of the first sheet and the second sheet were set to 4.8 cm×4.8 cm (area 23.0 cm²) in Example B10, 5.5 cm×5.5 cm (area 30.3 cm²) in Example B11, and 3.9 cm×3.9 cm (area 15.2 cm²) in Comparative Example B1, the steam generating portions 121 were disposed between the respective sheets, and the peripheral edge portions were hermetically sealed to obtain the steam generators 120. The steam heating mask 100 was prepared in the same manner as in Example B1 except that, so that the area ratio of the steam generator 120 with respect to the area of the entire surface of the mask body portion 101 on the side of the wearer was set as shown in Table 4.

Examples B12, B13 and Comparative Example B2

In the preparation of the steam generating portion 121, when die-coating the heat generation composition on one side of the base material layer 121B, the size of one of the steam generating portions 121 was set to 4.9 cm×6.5 cm (area 31.9 cm²) in Example B12, 4.9 cm×7.5 cm (area 36.8 cm²) in Example B13, and 4.9 cm×8.5 cm (area 41.7 cm²) in Comparative Example B2, and the heat generation composition was prepared so that the coating amount of the heat generation composition has the same thickness (1.4 g when converted per 4.9 cm×4.9 cm) as that in Example B1. In addition, in the preparation of the steam generator, the sizes of the first sheet and the second sheet were set to 6.3 cm×8.4 cm (area 52.9 cm²) in Example B12, 6.3 cm×9.6 cm (area 60.5 cm²) in Example B13, and 6.4 cm×10.6 cm (area 67.8 cm²) in Comparative Example B2, the steam generating portions 121 were disposed between the respective sheets, and the peripheral edge portions were hermetically sealed to obtain the steam generators 120. The steam heating mask 100 was prepared in the same manner as in Example B1 except that, so that the area ratio of the steam generator 120 with respect to the area of the entire surface of mask body portion 101 on the side of the wearer was set as shown in Table 4.

Examples B14 and B15

A steam generator 120 was prepared according to Example B1, except that only one layer of the steam generating portion 121 used in Example B1 was used as the steam generating portion, and the first sheet having a degree of air permeability shown in Table 4 was used. In the Example B14, a steam heating mask 100 was prepared in the same manner as in Example B1 except that. In the Example B15, a steam heating mask 100 was prepared by laminating one sheet of ADVANTEC (registered trademark) qualitative filter paper No. 2 cut to a size of 63 mm square so as to be in contact with the second sheet of the steam generator in addition to the prepared steam generator at the time of preparing a steam heating mask.

Example B16

A powdery heat generation composition having the composition shown in Table 2 was prepared as a steam generating portion by the following procedure. In a nitrogen stream, iron powder, water, salt, water absorbing polymer, and activated carbon were mixed until uniform, and a powdery steam generating portion was prepared. In the preparation of the steam generator 120, the steam heating mask 100 was prepared in the same manner as in Example B1, except that 2.8 g of the powdery steam generating portion was used instead of the sheet-like steam generating portion 121 in Example B1.

Comparative Examples B3 and B4

A steam heating mask 100 was prepared in the same manner as in Example B1, except that a calcium carbonate-containing polyethylene film having the degree of air permeability shown in Table 4 and a basis weight of 50 g/m², TSF-EU, and manufactured by Kohjin Co., Ltd. was used as the first sheet 122A and the second sheet 122B of the steam generator 120.

The oxygen blocking bag (packaging material) was opened, the prepared steam generator 120 was taken out, quickly set on the mask 110, and the same evaluation as in Example A was performed. The results are shown in Table 4.

TABLE 4

| | Physical properties | Example | | | | | | | | | |
|---|---|---|---|---|---|---|---|---|---|---|---|
| | | B1 | B2 | B3 | B4 | B5 | B6 | B7 | B8 | B9 | B10 |
| Steam generator | Degree of air permeability (sec/100 ml) of first sheet 122A (skin side sheet) | 0.0 | 1.0 | 8.1 | 250 | 0.0 | 0.0 | 0.0 | 0.0 | 0.0 | 0.0 |
| | Degree of air permeability (sec/100 ml) of second sheet 122B (outside sheet) | 7000 | 7000 | 7000 | 7000 | 8000 | 3000 | 4000 | 2500 | 250 | 7000 |
| | Type of steam generation portion | Coated type (2 sheets) | ← | ← | ← | ← | ← | ← | ← | ← | ← |
| | Area of steam generation portion (cm²) | 24.0 | ← | ← | ← | ← | ← | ← | ← | ← | 10.9 |

TABLE 4-continued

|  |  |  |  |  |  |  |  |  |  |  |  |
|---|---|---|---|---|---|---|---|---|---|---|---|
|  | Area of steam generator (cm²) | 39.7 | 39.7 | 39.7 | 39.7 | 39.7 | 39.7 | 39.7 | 39.7 | 39.7 | 23.0 |
|  | Stiffness value (gf/60 mm width in a vertical direction) | 82.3 | 50.7 | 71.3 | 54.0 | 64.7 | 73.0 | 65.7 | 71.7 | 70.3 | 39.7 |
|  | Steam generation amount (mg/cell · 10 min) | 394 | 364 | 336 | 368 | 413 | 425 | 426 | 359 | 408 | 144 |
|  | Steam generation amount (mg/cm² · 10 min) | 9.9 | 9.2 | 8.5 | 9.3 | 10.4 | 10.7 | 10.7 | 9.1 | 10.3 | 6.3 |
| Steam heating mask | Area ratio of steam generator | 52% | 52% | 52% | 52% | 52% | 52% | 52% | 52% | 52% | 30% |
|  | Swelling of steam heating mask (ml, one cell · 30 minutes later) | 0.0 | 0.0 | 0.0 | 13.0 | 0.0 | 0.0 | 0.0 | 0.0 | 0.0 | 0.0 |
|  | Steam generation amount of steam heating mask (mg/10 min) | 789 | 728 | 671 | 736 | 826 | 851 | 852 | 719 | 815 | 288 |
|  | Maximum absolute humidity (g/m3)/using mannequin | 28.2 | 27.1 | 28.9 | 33.6 | 26.3 | 31.3 | 28.8 | 27.0 | 28.0 | 17.4 |
|  | Average absolute humidity (g/m3) for 10 minutes/using mannequin | 20.5 | 19.6 | 20.5 | 22.6 | 19.0 | 22.5 | 20.3 | 20.0 | 20.4 | 14.4 |
| Evaluation | Warm feeling | 3 | 3 | 3 | 4 | 3 | 4 | 4 | 3 | 4 | 2 |
|  | Durability | 2 | 2 | 2 | 3 | 2 | 2 | 2 | 2 | 1 | 1 |
|  | Steam feeling (moist feeling) | 5 | 5 | 5 | 5 | 5 | 5 | 5 | 5 | 4 | 3 |
|  | Feeling of Stuffiness | 5 | 5 | 5 | 4 | 5 | 5 | 5 | 5 | 5 | 5 |

|  | Physical properties | Example | | | | | | Comparative Example | | | |
|---|---|---|---|---|---|---|---|---|---|---|---|
|  |  | B11 | B12 | B13 | B14 | B15 | B16 | B1 | B2 | B3 | B4 |
| Steam generator | Degree of air permeability (sec/100 ml) of first sheet 122A (skin side sheet) | 0.0 | 0.0 | 0.0 | 250 | 250 | 0.0 | 0.0 | 0.0 | 1300 | 2500 |
|  | Degree of air permeability (sec/100 ml) of second sheet 122B (outside sheet) | 7000 | 7000 | 7000 | 7000 | 7000 | 7000 | 7000 | 7000 | 1300 | 1000 |
|  | Type of steam generation portion | ← | ← | ← | Coated type (1 sheet) | ← + Stiff body | Powder | Coated type (2 sheets) | ← | ← | ← |
|  | Area of steam generation portion (cm²) | 10.9 | 31.9 | 36.8 | 24.0 | ← | — | 10.9 | 41.7 | 21.0 | ← |
|  | Area of steam generator (cm²) | 30.3 | 52.9 | 60.5 | 39.7 | 39.7 | 39.7 | 15.2 | 67.8 | 39.7 | 39.7 |
|  | Stiffness value (gf/60 mm width in a vertical direction) | 39.7 | 87.0 | 82.7 | 25.3 | 119.0 | 36.7 | 45.0 | 92.3 | 41.0 | 39.3 |
|  | Steam generation amount (mg/cell · 10 min) | 144 | 523 | 565 | 153 | 153 | 257 | 139 | 598 | 262 | 252 |
|  | Steam generation amount (mg/cm² · 10 min) | 4.8 | 9.9 | 9.3 | 3.9 | 3.9 | 6.5 | 9.2 | 8.8 | 6.6 | 6.3 |
| Steam heating mask | Area ratio of steam generator | 40% | 70% | 80% | 52% | 52% | 52% | 20% | 90% | 52% | 52% |
|  | Swelling of steam heating mask (ml, one cell · 30 minutes later) | 0.0 | 0.0 | 0.0 | 9.0 | 6.0 | 0.0 | 0.0 | 0.0 | 20.0 | 17.0 |
|  | Steam generation amount of steam heating mask (mg/10 min) | 289 | 1046 | 1129 | 307 | 307 | 513 | 278 | 1196 | 524 | 503 |
|  | Maximum absolute humidity (g/m3)/using mannequin | 18.3 | 32.1 | 37.5 | 20.0 | 19.1 | 21.2 | 14.0 | 37.4 | 27.0 | 24.4 |
|  | Average absolute humidity (g/m3) for 10 minutes/using mannequin | 15.0 | 24.1 | 27.1 | 15.5 | 14.6 | 18.3 | 12.8 | 26.4 | 17.8 | 16.7 |
| Evaluation | Warm feeling | 2 | 3 | 4 | 3 | 3 | 3 | 1 | 5 | 3 | 3 |
|  | Durability | 1 | 2 | 2 | 1 | 1 | 2 | 1 | 2 | 2 | 2 |
|  | Steam feeling (moist feeling) | 3 | 5 | 5 | 3 | 3 | 4 | 2 | 5 | 4 | 3 |
|  | Feeling of Stuffiness | 5 | 5 | 4 | 4 | 5 | 5 | 5 | 2 | 1 | 2 |

The invention claimed is:

1. A steam heating mask comprising:
   a mask that includes a mask body portion covering a nose and a mouth of a wearer when wearing the mask, and a pair of ear hook portions provided at both left and right ends of the mask body portion; and
   a steam generator on the mask body portion,
   wherein a proportion of an area occupied by the steam generator is 30% to 80% with respect to an area of an entire surface of the mask body portion on a side in contact with the wearer when worn,
   the steam generator accommodates a steam generating portion therein,
   the steam generator includes a first sheet on a surface of the steam generating portion on the side in contact with the wearer when worn, and a second sheet on a surface, opposite to the surface on the side in contact with the wearer when worn, of the steam generating portion,
   a degree of air permeability of the first sheet is equal to or less than 7,000 sec/100 ml,
   a degree of air permeability of the second sheet is greater than 8,000 sec/100 ml, and
   wherein a maximum value of an absolute humidity in the mask during use of the steam heating mask is 12 g/m³ to 50 g/m³.

2. The steam heating mask according to claim 1,
wherein a stiffness value of the steam generator in a vertical direction is equal to or greater than 30 gf/60 mm width.

3. The steam heating mask according to claim 1,
wherein a maximum value of an absolute humidity in the mask during use of the steam heating mask is 13 g/m³ to 45 g/m³.

4. The steam heating mask according to claim 1,
wherein an air permeation resistance of the mask body portion is 5 Pa to 200 Pa.

5. A steam heating mask comprising:
a mask that includes a mask body portion covering a nose and a mouth of a wearer when wearing the mask, and a pair of ear hook portions provided at both left and right ends of the mask body portion; and
a steam generator on the mask body portion,
wherein a proportion of an area occupied by the steam generator is 30% to 80% with respect to an area of an entire surface of the mask body portion on a side in contact with the wearer when worn,
the steam generator accommodates a steam generating portion therein,
the steam generator includes a first sheet on a surface of the steam generating portion on the side in contact with the wearer when worn, and a second sheet on a surface, opposite to the surface on the side in contact with the wearer when worn, of the steam generating portion,
a degree of air permeability of the second sheet is 250 sec/100 ml to 8,000 sec/100 ml,
a degree of air permeability of the first sheet is equal to or less than 20% with respect to the degree of air permeability of the second sheet, and
wherein a maximum value of an absolute humidity in the mask during use of the steam heating mask is 12 g/m³ to 50 g/m³.

6. The steam heating mask according to claim 5,
wherein a stiffness value of the steam generator in a vertical direction is equal to or greater than 30 gf/60 mm width.

7. The steam heating mask according to claim 5,
wherein a maximum value of an absolute humidity in the mask during use of the steam heating mask is 13 g/m³ to 45 g/m³.

8. The steam heating mask according to claim 5,
wherein an air permeation resistance of the mask body portion is 5 Pa to 200 Pa.

* * * * *